US008421036B2

(12) United States Patent
Horii et al.

(10) Patent No.: US 8,421,036 B2
(45) Date of Patent: Apr. 16, 2013

(54) OPTICAL SIGNAL DETECTION METHOD, APPARATUS, SAMPLE CELL AND KIT

(75) Inventors: Kazuyoshi Horii, Ashigarakami-gun (JP); Toshihito Kimura, Ashigarakami-gun (JP)

(73) Assignee: FUJIFILM Corporation, Tokyo (JP)

( * ) Notice: Subject to any disclaimer, the term of this patent is extended or adjusted under 35 U.S.C. 154(b) by 1033 days.

(21) Appl. No.: 12/425,826

(22) Filed: Apr. 17, 2009

(65) Prior Publication Data

US 2009/0261269 A1 Oct. 22, 2009

(30) Foreign Application Priority Data

Apr. 18, 2008 (JP) .................... 2008-108949
Jan. 23, 2009 (JP) .................... 2009-012953

(51) Int. Cl.
*F21V 9/16* (2006.01)
(52) U.S. Cl.
USPC .............. 250/459.1; 250/458.1; 250/461.1
(58) Field of Classification Search ............... 250/458.1, 250/461.1, 459.1
See application file for complete search history.

(56) References Cited

U.S. PATENT DOCUMENTS

| 5,763,191 | A * | 6/1998 | Knoll et al. ............. 435/7.1 |
| 6,194,223 | B1 | 2/2001 | Herrmann et al. |
| 2003/0228682 | A1 | 12/2003 | Lakowicz et al. |
| 2004/0157237 | A1 | 8/2004 | Malak et al. |
| 2006/0181701 | A1 | 8/2006 | Tomaru |
| 2006/0234396 | A1 | 10/2006 | Tomita et al. |
| 2007/0118936 | A1 | 5/2007 | Matsunami |
| 2007/0158549 | A1 | 7/2007 | Naya et al. |

FOREIGN PATENT DOCUMENTS

WO 2007/129682 A1 11/2007

OTHER PUBLICATIONS

Kim et al., "Analysis of non-labeling protein array on biotin modified gold surfaces using atomic force microscopy and surface plasmon resonance," Jun. 7, 2007, Colloids and Surfaces, pp. 541-544.*
EP Communication, dated Jul. 30, 2009, issued in corresponding EP Application No. 09005481.8, 12 pages.
Ekgasit et al., "Fluorescence intensity in surface-plasmon field-enhanced fluorescence spectroscopy," Sensors and Actuators B, vol. 104, No. 2, Jan. 24, 2005, pp. 294-301, XP-025328640.
Yan et al., "Dye-doped nanoparticles for bioanalysis," Nanotoday, vol. 2, No. 3, Jun. 2007, pp. 44-50, XP-022063174.
Yu et al., "Surface Plasmon Fluorescence Immunoassay of Free Prostate-Specific Antigen in Human Plasma at the Femtomolar Level," Analytical Chemistry, vol. 76, No. 22, Nov. 15, 2004, pp. 6765-6770.

* cited by examiner

*Primary Examiner* — Christine Sung
(74) *Attorney, Agent, or Firm* — Sughrue Mion, PLLC

(57) ABSTRACT

A sensor chip includes a dielectric plate and a sensor portion having a metal layer deposited on a predetermined area on the dielectric plate. A photo-reactable labeling-substance of an amount corresponding to the amount of a substance to be detected in a sample binds to the sensor portion by contacting the sample with the sensor portion. The amount of the substance to be detected is obtained by irradiating the predetermined area with excitation light and by detecting light output from the photo-reactable labeling-substance in an enhanced electric field that has been generated on the metal layer by irradiation with the excitation light. The photo-reactable labeling-substance includes a photo-reactable substance enclosed by a light transmissive material that transmits light output from the photo-reactable substance to prevent metal quenching that occurs when the photo-reactable substance is located close to the metal layer.

20 Claims, 16 Drawing Sheets

OPTICAL SIGNAL DETECTION METHOD, APPARATUS, SAMPLE CELL AND KIT

BACKGROUND OF THE INVENTION

1. Field of the Invention

The present invention relates to an optical signal detection method for detecting a specific substance in a sample by detecting an optical signal output from a label. The optical signal detection method includes a fluorescence detection method for detecting a specific substance in a sample by detecting fluorescence. Further, the present invention relates to an optical signal detection apparatus, a sample cell for detecting an optical signal, and a kit for detecting an optical signal.

2. Description of the Related Art

Conventionally, in the field of bio-measurement or the like, a fluorescence detection method is widely adopted as a highly accurate and easy measurement method. In the fluorescence detection method, a sample that is supposed to include a detection target substance that outputs fluorescence by being excited by irradiation with light having a specific wavelength is irradiated with the excitation light having the specific wavelength. At this time, the fluorescence is detected to confirm the presence of the detection target substance. Further, when the detection target substance per se is not a phosphor (fluorescent substance), a substance that has been labeled with a fluorescent dye and that specifically binds to the detection target substance is placed in contact with the sample. Then, fluorescence from the fluorescent dye is detected in a manner similar to the aforementioned method, thereby confirming the presence of the bond between the detection target substance and the substance that specifically binds to the detection target substance. In other words, presence of the detection target substance is confirmed, and this method is widely adopted.

Further, in the fluorescence detection method as described above, a method utilizing an electronic field enhancement effect by plasmon resonance to improve the sensitivity of detection is proposed in U.S. Pat. No. 6,194,223 (Patent Literature 1) or the like. In the method disclosed in Patent Literature 1, a sensor chip including a metal layer (metal film, foil or coating) deposited in a predetermined area of a transparent support body is provided. Further, excitation light is caused to enter the interface between the support body and the metal layer at a predetermined angle greater than or equal to a total reflection angle. The excitation light is caused to enter the interface from a surface of the support body, the surface being opposite to the metal-layer-formed surface of the support body. Accordingly, surface plasmons are generated in the metal layer by irradiation with the excitation light. Consequently, fluorescence is enhanced by the electric field enhancement action by the surface plasmons, thereby improving the S/N (signal to noise) ratio.

However, in a surface-plasmon-enhanced fluorescence detection apparatus, when the fluorescent dye in the sample and the metal layer are too close to each other, a problem as described in F. Yu et al., "Surface Plasmon Fluorescence Immunoassay of Free Prostate-Specific Antigen in Human Plasma at the Femtomolar Level", Analytical Chemistry, Vol. 76, Issue 22, pp. 6765-1770, 2004 (Non-Patent Literature 1) may arise. Specifically, energy excited in the fluorescent dye transfers to the metal layer before fluorescence is produced by the energy excited in the fluorescent dye. Therefore, fluorescence may not be produced (so-called metal-quenching may occur).

Therefore, Non-Patent Literature 1 proposes a method of forming a carboxylmethyl dextran (CMD) coating on the metal layer to maintain a certain distance between the fluorescent dye and the metal layer.

However, in the method disclosed in Non-Patent Literature 1, when the CMD coating is formed on the metal layer, it is necessary to apply the CMD coating after an SAM (self-assembled monolayer) coating is applied to the metal layer. Therefore, longer time and additional steps are required to prevent metal-quenching. Further, it is difficult to control the position of the CMD coating to which the fluorescence-labeled substance is attached and to strictly control the distance between the fluorescent label and the metal layer. When the distance between the fluorescent label and the metal layer is not controlled as intended, the intensity of the fluorescent signal is greatly influenced, thereby deteriorating the reliability of the signal.

The problem of metal quenching and other problems arising therefrom are not limited to the case of using the fluorescent label. Similar problems also occur when a photo-reactable substance having a certain photo-reactable characteristic to light is used as a label.

SUMMARY OF THE INVENTION

In view of the foregoing circumstances, it is an object of the present invention to provide an optical signal detection method and apparatus that can effectively prevent metal quenching by using a simple method. Further, it is an object of the present invention to stably detect optical signals.

Further, it is an object of the present invention to provide a sample cell and a sample kit that are used in the optical signal detection method.

An optical signal detection method according to the present invention is an optical signal detection method comprising the steps of:

preparing a sensor chip including a dielectric plate and a sensor portion having a metal layer deposited on a predetermined area of a surface of the dielectric plate;

binding a binding substance of an amount corresponding to the amount of a substance to be detected that is included in a sample to the sensor portion by contacting the sample with the sensor portion of the sensor chip, the binding substance having a photo-reactable labeling-substance attached to the binding substance; and obtaining the amount of the substance to be detected by irradiating the predetermined area with excitation light and by detecting light output from the photo-reactable labeling-substance in an enhanced electric field that has been generated on the metal layer by irradiation with the excitation light, wherein the photo-reactable labeling-substance includes a plurality of molecules of a photo-reactable substance enclosed (encapsulated) by a light transmissive material that transmits light output from the plurality of molecules of the photo-reactable substance to prevent metal quenching that occurs when the photo-reactable substance is located close to the metal layer.

Here, the "binding substance" may be a substance that binds to the sensor portion through the substance to be detected. Alternatively, the "binding substance" may be a substance that binds to the sensor portion in competition with the substance to be detected. For example, in an optical signal detection method for detecting an antigen-antibody reaction, when the antigen is a substance to be detected and an assay is performed by a sandwich method, an immobilized layer is composed of a primary antibody (immobilized antibody) that specifically binds to the antigen, and the binding substance is composed of a secondary antibody that specifically binds to the antigen. Further, when an assay is performed by a competition method, the binding substance is composed of a competing antigen that competes with the antigen and binds to the immobilized antibody. As described above, the optical signal detection method of the present method may be adopted in an assay using a sandwich method and in an assay using a competition method.

The expression "obtaining the amount of the substance to be detected" means detecting presence of the substance to be detected. Further, the amount of the substance to be detected may mean not only the quantitative amount of the substance to be detected but the qualitative value of the substance to be detected.

The photo-reactable labeling-substance has particle form, and includes a plurality of molecules of a photo-reactable substance enclosed by a light transmissive material. A part of the plurality of molecules of the photo-reactable substance may be exposed to the outside of the light transmissive material. Further, the distribution condition of the plurality of molecules of a photo-reactable substance in the light transmissive material may be in any manner. The plurality of molecules of the photo-reactable substance may be distributed uniformly (evenly). Alternatively, the plurality of molecules of the photo-reactable substance may be distributed unevenly. Further, at a center region of the photo-reactable labeling-substance that has particle form, a region including no photo-reactable substance may be present.

Here, the "photo-reactable substance" should have a photo-reactable characteristic with respect to excitation light. The photo-reactable substance is not limited to a fluorescent dye molecule, a fluorescent microparticle (particle), and a quantum dot molecule (semiconductor microparticle or particle), which produce fluorescence by irradiation with the excitation light. The "photo-reactable substance" or the "molecules of the photo-reactable substance" may be a metal microparticle (particle) that produces scattered light by irradiation with the excitation light. Therefore, the "light output from the plurality of molecules of the photo-reactable substance" may be light (fluorescence, phosphorescence or the like) produced and output from the photo-reactable substance by irradiation with the excitation light. Alternatively, the "light output from the plurality of molecules of the photo-reactable substance" may be light (scattered light) that scatters from the plurality of molecules of the photo-reactable substance by irradiation with the excitation light.

In the optical signal detection method of the present invention, the light output from the photo-reactable labeling-substance may be detected only once after a predetermined time period has passed from the start of binding and the amount of the substance to be detected may be obtained based on the intensity of the light. However, it is more desirable that the light output from the photo-reactable labeling-substance is detected at a plurality of different points in time after the start of binding and the amount of the substance to be detected is obtained based on a temporal change in the intensity of the light.

Here, "a plurality of different points in time" may be a plurality of different points in time at regular intervals. Alternatively, the intervals of the plurality of different points in time may be different from each other. Further, the different points in time may be continuous points. The number of the plurality of different points in time may be any number greater than or equal to 2. However, it is desirable that the number of the plurality of different points is greater, in other words, detection is performed at a greater number of different points in time to improve the accuracy in measurement.

Here, the particle diameter of the photo-reactable labeling-substance may be less than or equal to 5300 nm. Optionally, the particle diameter of the photo-reactable labeling-substance may be in the range of 70 nm to 900 nm. Further, when the photo-reactable substance produces fluorescence by irradiation with the excitation light, the particle diameter of the photo-reactable labeling-substance maybe in the range of 90 nm to 700 nm. Optionally, the particle diameter of the photo-reactable labeling-substance may be in the range of 130 nm to 500 nm. Further, in the specification of the present application, when the photo-reactable labeling-substance has substantially spherical form, the particle diameter of the photo-reactable labeling-substance is the diameter of the photo-reactable labeling-substance. When the photo-reactable labeling-substance does not have spherical form, the particle diameter of the photo-reactable labeling-substance may be defined by an average length of the maximum width and the minimum width of the photo-reactable labeling-substance.

Further, when the photo-reactable substance produces fluorescence by irradiation with the excitation light, a metal coating may be provided on the surface of the photo-reactable labeling-substance in such a manner that the thickness of the metal coating is sufficiently thin to transmit the fluorescence.

Further, an optical signal detection apparatus according to the present invention is an optical signal detection apparatus comprising:

a sensor chip including a dielectric plate and a sensor portion having a metal layer deposited on a predetermined area of a surface of the dielectric plate;

an excitation-light irradiation optical system that irradiates the predetermined area with excitation light;

a light detection means, wherein when a sample is contacted with the sensor portion, if a binding substance of an amount corresponding to the amount of a substance to be detected that is included in the sample binds to the sensor portion, the binding substance having a photo-reactable labeling-substance attached to the binding substance, the light detection means detects light output from the photo-reactable labeling-substance in an enhanced electric field that has been generated on the metal layer by irradiating the sensor chip with the excitation light, and wherein the photo-reactable labeling-substance includes a plurality of molecules of a photo-reactable substance enclosed by a light transmissive material that transmits light output from the plurality of molecules of the photo-reactable substance to prevent metal quenching that occurs when the photo-reactable substance is located close to the metal layer.

Further, a sample cell for detecting an optical signal according to the present invention is a sample cell for detecting an optical signal, wherein the sample cell is used in an optical signal detection method for detecting light output from a photo-reactable labeling-substance, the sample cell comprising:

a base having a flow path (channel) through which a liquid sample flows down;

an injection opening for injecting the liquid sample into the flow path, the injection opening being provided on the upstream side of the flow path;

an air hole for causing the liquid sample injected from the injection opening to flow toward the downstream side of the flow path, the air hole being provided on the downstream side of the flow path;

a sensor chip portion provided in the flow path between the injection opening and the air hole, the sensor chip portion including a dielectric plate that is provided on at least a part of the inner wall of the flow path and a metal layer that is provided in a predetermined area on a sample-contact-side surface of the dielectric plate;

a first binding substance immobilized on the metal layer, the first binding substance specifically binding to a substance to be detected; and a photo-reactable labeling-substance immobilized at a position in the flow path, the position being on the upstream side of the sensor chip portion, and wherein the photo-reactable labeling-substance is modified with a second binding substance that specifically binds to the substance to be detected or by a third binding substance that specifically binds to the first binding substance and that competes with the substance to be detected.

Further, when the sample cell according to the present invention includes a photo-reactable labeling-substance modified with a second binding substance, the sample cell is suitable for an assay using the sandwich method. Alternatively, when the sample cell according to the present invention includes a photo-reactable labeling-substance modified with a third binding substance, the sample cell is suitable for an assay using the competition method.

Further, a kit for detecting an optical signal according to the present invention is a kit for detecting an optical signal, wherein the kit is used in an optical signal detection method for detecting light output from a photo-reactable labeling-substance, the kit comprising:

a sample cell; and a solution for labeling, and wherein the sample cell includes:

a base having a flow path through which a liquid sample flows down;

an injection opening for injecting the liquid sample into the flow path, the injection opening being provided on the upstream side of the flow path;

an air hole for causing the liquid sample injected from the injection opening to flow toward the downstream side of the flow path, the air hole being provided on the downstream side of the flow path;

a sensor chip portion provided in the flow path between the injection opening and the air hole, the sensor chip portion including a dielectric plate that is provided on at least a part of the inner wall of the flow path and a metal layer that is provided in a predetermined area on a sample-contact-side surface of the dielectric plate; and a first binding substance immobilized on the metal layer, the first binding substance specifically binding to a substance to be detected, and wherein when optical signal detection is performed, the solution for labeling is caused to flow down through the flow path together with the liquid sample or after the liquid sample flows down through the flow path, and wherein the solution for labeling contains a photo-reactable labeling-substance modified with a second binding substance that specifically binds to the substance to be detected or by a third binding substance that specifically binds to the first binding substance and that competes with the substance to be detected.

Further, when the kit for detecting an optical signal according to the present invention includes a photo-reactable labeling-substance modified with a second binding substance, the kit is suitable for an assay using the sandwich method. Alternatively, when the kit for detecting an optical signal according to the present invention includes a photo-reactable labeling-substance modified with a third binding substance, the kit is suitable for an assay using the competition method.

Further, in the sample cell for detecting an optical signal according to the present invention and in the kit for detecting an optical signal according to the present invention, the "photo-reactable labeling-substance modified with a second or third binding substance" refers to a substance in which a photo-reactable labeling-substance and a binding substance are combined together or united. Further, in the optical signal detection method and apparatus of the present invention, the "binding substance having a photo-reactable labeling-substance attached to the binding substance" refers to a substance in which a photo-reactable labeling-substance and a binding substance are combined together or united.

Further, the "photo-reactable labeling-substance" in the sample cell for detecting an optical signal according to the present invention and in the kit for detecting an optical signal according to the present invention and the "photo-reactable labeling-substance" in the optical signal detection method and apparatus of the present invention are the same. The "photo-reactable labeling-substance" includes a plurality of molecules of a photo-reactable substance enclosed (encapsulated) by a light transmissive material that transmits light output from the plurality of molecules of the photo-reactable substance to prevent metal quenching that occurs when the photo-reactable substance is located close to the metal layer.

Here, the particle diameter of the photo-reactable labeling-substance may be less than or equal to 5300 nm. Optionally, the particle diameter of the photo-reactable labeling-substance may be in the range of 70 nm to 900 nm. Further, when the photo-reactable substance produces fluorescence by irradiation with the excitation light, the particle diameter of the photo-reactable labeling-substance maybe in the range of 90 nm to 700 nm. Optionally, the particle diameter of the photo-reactable labeling-substance may be in the range of 130 nm to 500 nm.

Further, when the photo-reactable substance produces fluorescence by irradiation with the excitation light, a metal coating may be provided on the surface of the photo-reactable labeling-substance in such a manner that the thickness of the metal coating is sufficiently thin to transmit the fluorescence.

Here, the metal layer deposited on the dielectric plate should generate surface plasmons or localized plasmons by irradiation with excitation light. The metal layer may be formed by a metal coating (foil or film). Alternatively, the metal layer may be formed by a metal fine structure having an uneven pattern on the surface thereof, the uneven pattern having a cycle shorter than the wavelength of the excitation light. Alternatively, the metal layer may be formed by a plurality of metal nano-rods having a size smaller than the wavelength of the excitation light. As the material of the metal layer, a material containing, as a main component, at least one metal selected from the group consisting of Au, Ag, Cu, Al, Pt, Ni, Ti and alloys of these metals is desirable. Here, the term "main component" is defined as a component the content of which is 90% by mass or greater.

In the optical signal detection method and apparatus of the present invention, the photo-reactable labeling-substance including a plurality of molecules of a photo-reactable substance enclosed by a light transmissive material that transmits light output from the plurality of molecules of the photo-reactable substance to prevent metal quenching that occurs when the photo-reactable substance is located close to the metal layer is used. Therefore, even if a coating (film) for preventing metal quenching is not provided on the metal layer, it is possible to maintain a certain distance between the metal layer and the photo-reactable substance. In other words, the metal layer and the photo-reactable substance are apart from each other by a certain distance. Therefore, it is possible to omit formation of a CMD coating and an SAM coating, which were conventionally necessary to prevent metal quenching, thereby reducing work and process. Further, it is possible to effectively prevent metal quenching by using a very simple method. Further, it is possible to stably detect a fluorescent signal.

Further, the sample cell of the present invention includes a photo-reactable labeling-substance immobilized at a position in the flow path, the position being on the upstream side of the sensor chip. The photo-reactable labeling-substance is modified with a second binding substance that specifically binds to the substance to be detected or by a third binding substance that specifically binds to the first binding substance and that competes with the substance to be detected. Further, the photo-reactable labeling-substance includes a plurality of molecules of a photo-reactable substance enclosed by a light transmissive material that transmits light output from the plurality of molecules of the photo-reactable substance to prevent metal quenching that occurs when the photo-reactable substance is located close to the metal layer. Therefore, even if a coating for preventing metal quenching is not provided on the metal layer, it is possible to maintain a certain distance between the metal layer and the photo-reactable substance. In other words, the metal layer and the photo-reactable substance are apart from each other by a certain distance. Therefore, it is possible to omit formation of a CMD coating and an SAM coating, which were conventionally necessary to prevent metal quenching, thereby reducing work or process. Further, it is possible to effectively prevent metal quenching by using a very simple method. Further, it is possible to stably detect a fluorescent signal.

Further, the sample kit according to the present invention includes a solution for labeling. The solution for labeling is caused to flow down through the flow path together with the liquid sample or after the liquid sample flows down through the flow path. The solution for labeling contains a photo-reactable labeling-substance modified with a second binding substance that specifically binds to the substance to be detected or by a third binding substance that specifically binds to the first binding substance and that competes with the substance to be detected. Further, the photo-reactable labeling-substance includes a plurality of molecules of a photo-reactable substance enclosed by a light transmissive material that transmits light output from the plurality of molecules of the photo-reactable substance to prevent metal quenching that occurs when the photo-reactable substance is located close to the metal layer. Therefore, even if a coating for preventing metal quenching is not provided on the metal layer, it is possible to maintain a certain distance between the metal layer and the photo-reactable substance. In other words, the metal layer and the photo-reactable substance are apart from each other by a certain distance. Therefore, it is possible to omit formation of a CMD coating and an SAM coating, which were conventionally necessary to prevent metal quenching, thereby reducing work or process. Further, it is possible to effectively prevent metal quenching by using a very simple method. Further, it is possible to stably detect a fluorescent signal.

DESCRIPTION OF THE PREFERRED EMBODIMENTS

<Embodiment 1>

Figure 1:
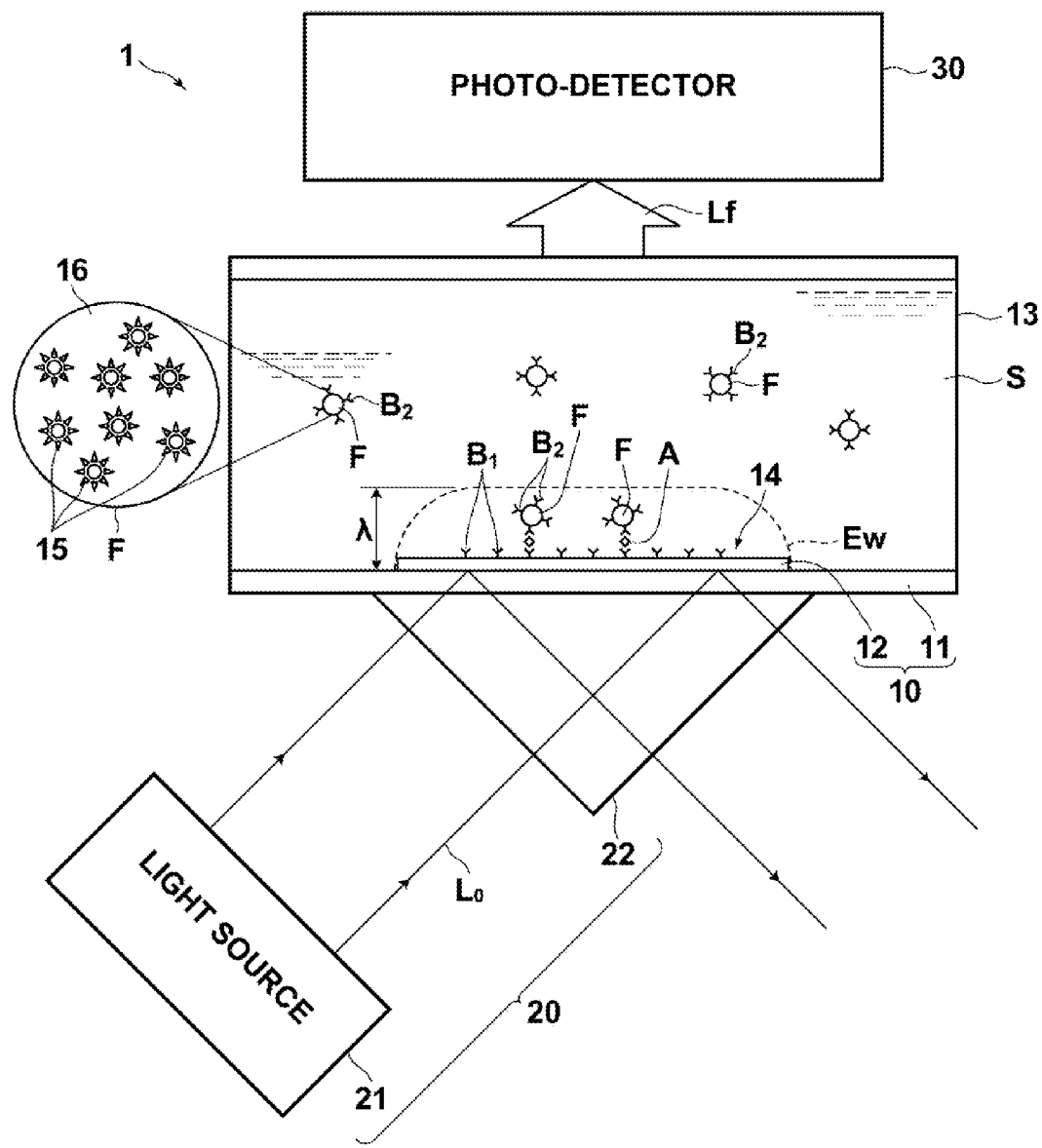
FIG. 1 is a schematic diagram illustrating the structure of an apparatus that is used in an optical signal detection method according to a first embodiment of the present invention.

An optical signal detection method according to a first embodiment of the present invention and an optical signal detection apparatus used for the method will be described with reference to the drawings. FIG. 1 is a diagram illustrating the whole apparatus. Each diagram is illustrated in such a manner that the size of each unit or element differs from the actual size thereof for the purpose of explanation.

An optical signal detection apparatus 1 illustrated in FIG. 1 includes a sensor chip 10 including a dielectric plate 11 and a metal layer (film, foil or coating) 12 deposited on a predetermined area of a surface of the dielectric plate 11, and the sensor chip 10 has a sensor portion 14. Further, the optical signal detection apparatus 1 includes an excitation-light irradiation optical system 20 that outputs excitation light $L_0$ and causes the excitation light $L_0$ to enter the interface between the dielectric plate 11 and the metal layer 12 at an angle satisfying total reflection condition. The excitation light is caused to enter the interface from a surface of the sensor chip 10, the surface being opposite to the metal-layer-formed surface of the sensor chip 10. Further, the optical signal detection apparatus 1 includes a photo-detector 30. When a sample is contacted with the metal layer 12, if binding substance $B_2$ having photo-reactable labeling-substance F attached to the binding substance is present in the sample, the photo-detector detects light Lf output from the photo-reactable labeling-substance F.

The excitation-light irradiation optical system 20 includes a light source 21, such as a semiconductor laser (LD), which outputs the excitation light $L_0$. Further, the excitation-light irradiation optical system 20 includes a prism 22 arranged in such a manner that a surface of the prism 22 contacts with the dielectric plate 11. The prism 22 guides the excitation light $L_0$ into the dielectric plate 11 so that the excitation light $L_0$ totally reflects at the interface between the dielectric plate 11 and the metal layer 12. Further, the prism 22 and the dielectric plate 11 are in contact with each other through refractive-index-matching oil. The light source 21 is arranged in such a manner that the excitation light $L_0$ enters the prism from another surface of the prism 22 and enters a sample-contact-surface 10a of the sensor chip 10 at an angle greater than or equal to a total reflection angle. Further, the light source 21 is arranged in such a manner that the excitation light $L_0$ enters the metal layer at a specific angle that generates surface plasmon resonance. Further, a light guide member may be arranged between the light source 21 and the prism 22, if necessary. Further, the excitation light $L_0$ is caused to enter the interface between the dielectric plate 11 and the metal layer 12 at p—polarized light so as to generate surface plasmons.

In the present embodiment, a sample retainer 13 for retaining (holding) liquid sample S is provided on the sensor chip 10. The sensor chip 10 and the sample retainer 13 together form a box-form cell that can retain the liquid sample. When a small amount of liquid sample that can remain on the sensor chip 10 by surface tension is measured, it is not necessary that the sample retainer 13 is provided.

The sensor chip 10 includes the dielectric plate 11 and the metal layer 12, made of a metal coating (film or foil). The metal layer 12 is deposited in a predetermined area of a surface of the dielectric plate 11, such as glass plate. The metal layer 12 may be deposited by using a known vapor-deposition method (evaporation method). The metal layer 12 is deposited by forming a mask having an opening on a surface of the dielectric plate 11. The opening of the mask is provided in the predetermined area of the surface of the dielectric plate 11. It is desirable that the thickness of the metal layer 12 is appropriately determined, based on the material of the metal layer 12 and the wavelength of the excitation light $L_0$, so that strong surface plasmons are excited. For example, when a laser beam that has a center wavelength of 780 nm is used as the excitation light and a gold (Au) film is used as the metal layer, it is desirable that the thickness of the metal layer 12 is 50 nm±20 nm. Optionally, the thickness of the metal layer 12 may be 47 nm±10 nm. Further, it is desirable that the metal layer contains, as a main component, at least one metal selected from the group consisting of Au, Ag, Cu, Al, Pt, Ni, Ti and alloys of these metals.

Next, as the optical signal detection method, a fluorescence detection method will be described. Here, the optical signal detection apparatus according to the present embodiment, illustrated in FIG. 1, is used as a fluorescence detection apparatus. In the following descriptions, a fluorescence labeling substance is used as the photo-reactable labeling-substance F, and fluorescence is detected as the optical signal.

The principle of fluorescence detection using the fluorescence detection apparatus (optical signal detection apparatus) 1 will be described.

When the excitation-light irradiation optical system 20 causes the excitation light $L_0$ to enter the interface between the dielectric plate 11 and the metal layer 12 at a specific angle greater than or equal to a total reflection angle, evanescent wave Ew penetrates into sample S on the metal layer 12. Further, surface plasmons are excited in the metal layer 12 by the evanescent wave Ew, and the surface plasmons generate electric field distribution on the surface of the metal layer 12, thereby forming an enhanced electric field region (area). At this time, when the fluorescence labeling substance F, which is the photo-reactable labeling-substance, is present in the portion of the sample S into which the evanescent wave Ew has penetrated, the fluorescence labeling substance F is excited, and fluorescence is produced. Here, the fluorescence is enhanced by the electric field enhancement effect of the surface plasmons that are present in the region (area) that is substantially similar to the region (area) into which the evanescent wave Ew has penetrated. Meanwhile, the fluorescence labeling substance F that is present outside of the region into which the evanescent wave Ew has penetrated is not excited, thereby producing no fluorescence. The photo-detector 30 (specifically, the fluorescence detector in this case) detects the enhanced fluorescence.

In the fluorescence detection method of the present embodiment, a fluorescence labeling substance that includes a fluorescent dye molecule 15, which is a photo-reactable substance, and a light transmissive material 16 is used as the fluorescence labeling substance F. The light transmissive material 16 transmits fluorescence produced by the fluorescent dye molecule. Further, the light transmissive material 16 encloses (encapsulates) the fluorescent dye molecule 15 to prevent metal quenching that occurs when the fluorescent dye molecule is located close to the metal layer. In the fluorescence labeling substance F, the fluorescent dye molecule is covered by the light transmissive material 16. Therefore, even if a coating for preventing metal quenching is not provided on the metal layer, it is possible to keep a certain distance between the metal layer and the fluorescent dye molecule. Further, it is possible to effectively prevent metal quenching by using a very simple method. Further, it is possible to stably detect a fluorescence signal. Further, as the photo-reactable substance, a fluorescent microparticle (particle), a quantum dot molecule (semiconductor microparticle or particle), or metal microparticle may be used instead of the fluorescent dye molecule. When the metal microparticle is provided as the photo-reactable substance, the photo-reactable labeling-substance outputs scattered light instead of the fluorescence by irradiation with the excitation light. However, it is possible to prevent metal quenching of the scattered light in a manner similar to the case of the fluorescence light when the fluorescent dye molecule is provided. Further, it is possible to stably detect a signal by the scattered light.

Further, in the present embodiment, the fluorescence labeling substance F includes a plurality of fluorescent dye molecules 15 that are enclosed. Therefore, when the fluorescence labeling substance F of the present embodiment is compared with a conventional fluorescent dye molecule 15 per se, which is a single molecule, it is possible to greatly increase the amount of produced fluorescence.

It is desirable that the particle diameter of the fluorescence labeling substance (photo-reactable labeling-substance) F is less than or equal to 5300 nm. Optionally, the particle diameter may be in the range of 70 nm to 900 nm. Further optionally, the particle diameter of the photo-reactable labeling-substance may be in the range of 130 nm to 500 nm. An example of the light transmissive material 16 is a dielectric, such as polystyrene and $SiO_2$. However, the light transmissive material 16 is not limited as long as the light transmissive material 16 can enclose (encapsulate) the fluorescent dye molecules 15, and transmit the fluorescence from the fluorescent dye molecules 15 to output the fluorescence to the outside of the fluorescence labeling substance F, and prevent metal quenching by the fluorescent dye molecules 15.

As described above, when the photo-reactable substance, such as the fluorescent dye molecules, in the sample is located too close to the metal layer, quenching occurs as energy is transferred to the metal. The degree of energy transfer is in inverse proportion to the cube of the distance when metal is a flat plate that has a semi-finite thickness. When the metal is an infinitely thin flat plate, the degree of energy transfer is in inverse proportion to the fourth power of the distance. When the metal is a microparticle, the degree of energy transfer is in inverse proportion to the sixth power of the distance. Therefore, it is desirable that the distance between the metal layer 12 and the photo-reactable substance is at least a few nm. Optionally, the distance may be 10 nm or greater.

Meanwhile, the photo-reactable substance is excited by the evanescent wave that has penetrated to the surface of the metal layer, and which has been enhanced by the surface plasmons. It is known that the reaching range of the evanescent wave (distance from the surface of the metal layer) is approximately wavelength $\lambda$ of the excitation light, and that the intensity of the electric field exponentially and sharply attenuates according to the distance from the surface of the metal. Since it is desirable that the intensity of the electric field that excites the photo-reactable substance is high as possible, it is desirable that the distance between the surface of the metal layer and the photo-reactable substance is less than 10 nm to effectively excite the photo-reactable substance.

When the fluorescence labeling substance F of the present embodiment is used, the fluorescent dye molecules 15 do not directly touch the metal layer, because the fluorescent dye molecules 15 are covered by the light transmissive material 16. Further, since a plurality of fluorescent dye molecules are enclosed (encapsulated) in the fluorescence labeling substance, it is possible to easily realize a state in which a plurality of fluorescent dye molecules are present at a distance in a range of within 10 to 100 nm from the metal layer. Further, it is not necessary to carry out complex process of providing the SAM coating or the CMD coating to prevent metal quenching.

Next, sensing using the fluorescence detection method will be described. In the fluorescence detection method, the optical signal detection apparatus 1, which is structured as described above, is used.

First, sample S, which is an assay target (examination target or analyte), is contacted with the sensor portion 14, which includes the metal layer 12 of the sensor chip 10. Here, a case of detecting antigen A, as a substance to be measured, which is contained in the sample S, will be described as an example. The surface of the metal layer 12 is modified with primary antibody $B_1$, as the first binding substance, which specifically binds to the antigen A. The sample S is poured into the sample retainer 13. Then, fluorescence labeling substance F the surface of which has been modified with secondary antibody $B_2$, as the second binding substance, which specifically binds to the antigen A, is poured into the sample retainer 13 in a similar manner. In this case, the primary antibody $B_1$, with which the surface of the metal layer 12 is modified, and the secondary antibody $B_2$, with which the surface of the fluorescence labeling substance F is modified, are selected in such a manner that they bind to different sites of the antibody A, which is the substance to be detected. After then, excitation light $L_0$ is output from the excitation light irradiation optical system 20 toward the predetermined area of the dielectric plate 11. Further, the fluorescence detector 30 detects fluorescence. At this time, when the fluorescence detector 30 detects predetermined fluorescence, it is judged that bond between the secondary antibody $B_2$ and the antigen A, in other words, the presence of the antigen A in the sample is confirmed.

Further, the timing of labeling the substance to be detected (antigen A) is not particularly limited. A fluorescence labeling substance may be added to the sample in advance before the substance to be detected (antigen A) is bound to the first binding substance (primary antibody $B_1$).

Further, the fluorescence labeling substance F that is used in the present embodiment may be produced in the following manner.

First, polystyrene particles (Estapor, $\phi$500 nm, 10% solid, carboxyl radical, product number K1-050) are prepared to produce 0.1% solid in phosphate (polystyrene solution: pH 7.0).

Next, 1 mL of ethyl acetate solution containing 0.3 mg of fluorescent dye (Molecular Probes, BODIPY-FL-SE, product number D2184) is produced.

The polystyrene solution and the solution containing the fluorescent dye are mixed together. Further, impregnation is effected together with evaporation. After then, the mixture is centrifuged (15000 rpm, 4° C., twice, 20 minutes each), and the supernatant is removed. Through the aforementioned process, it is possible to obtain the fluorescence labeling substance F containing a fluorescent dye that is enclosed by polystyrene, which has a metal-quenching prevention function. The particle diameter of the fluorescence labeling substance F that has been produced by impregnating the fluorescent dye into the polystyrene particles through the aforementioned process is the same as the diameter of the polystyrene particle (in the above example, φ500 nm).

<Embodiment 2>

Figure 2:
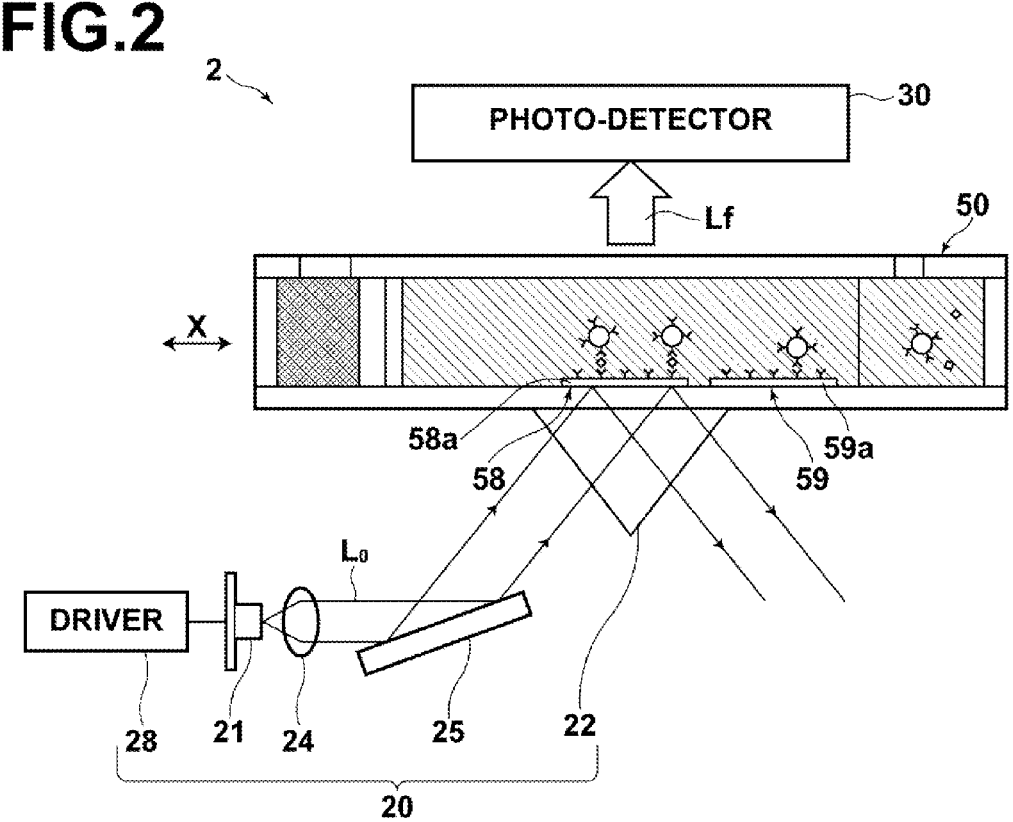
FIG. 2 is a schematic diagram illustrating the structure of an apparatus that is used in an optical signal detection method according to a second embodiment of the present invention.
Figure 3A:
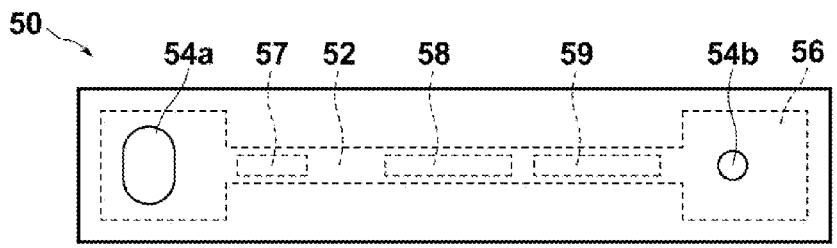
FIG. 3A is a plan view illustrating a sample cell in the first embodiment of the present invention.
Figure 3B:
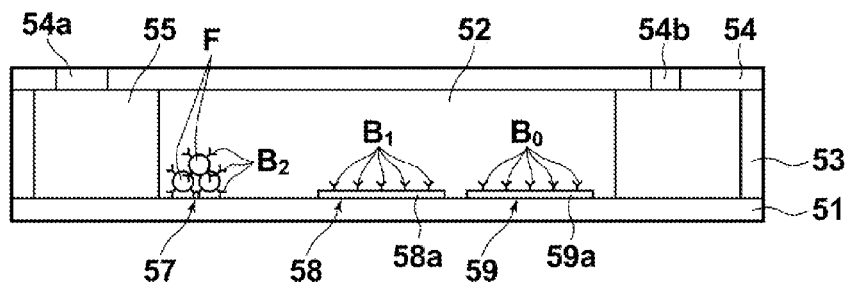
FIG. 3B is a side-sectional view of the sample cell illustrated in FIG. 3A.
Figure 4:
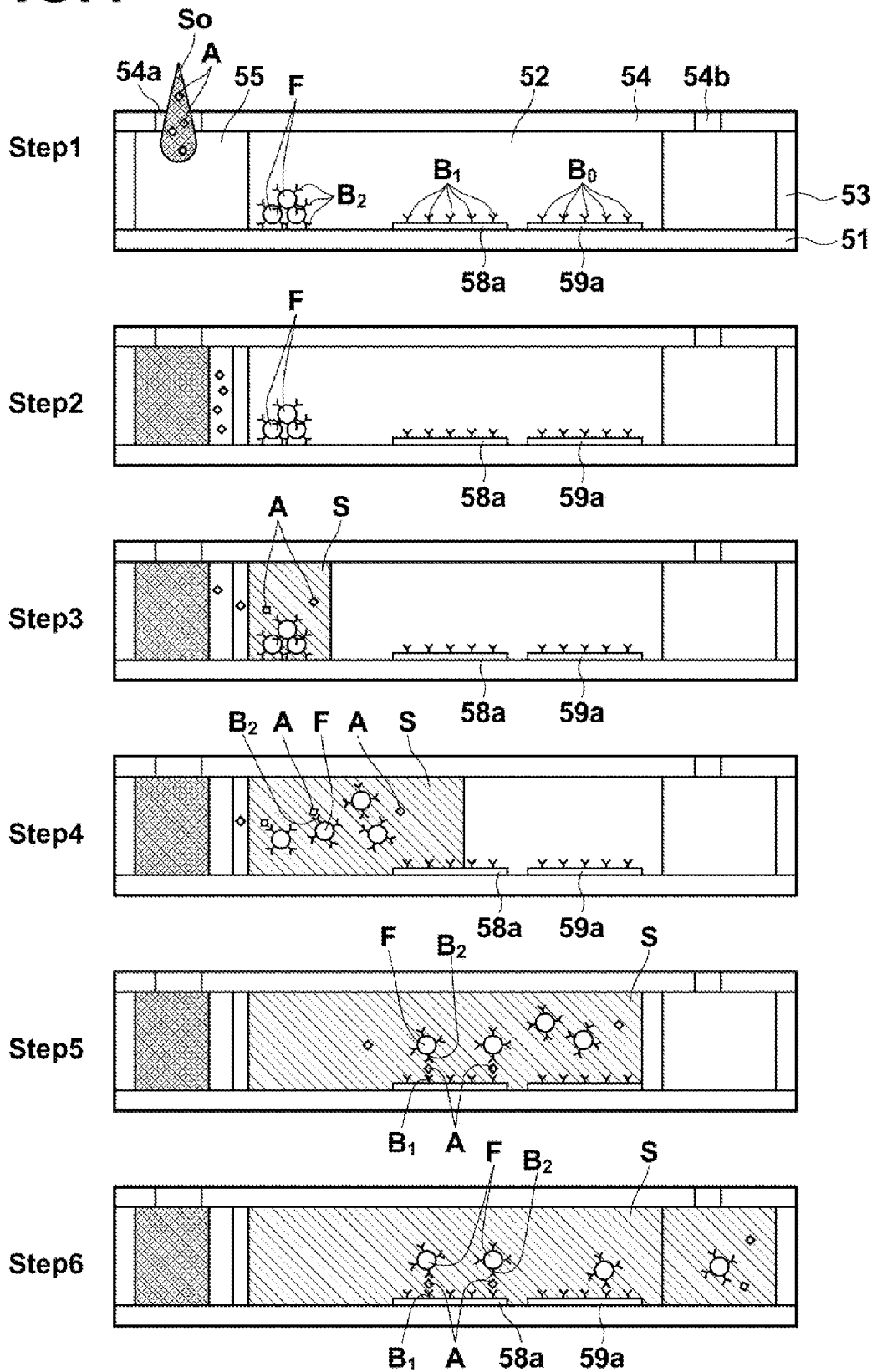
FIG. 4 is a diagram illustrating procedures of an assay in the optical signal detection apparatus according to the second embodiment of the present invention.

With reference to FIGS. 2 through 4, an optical signal detection method and apparatus according to a second embodiment of the present invention will be described. In the second embodiment, the same reference numerals are assigned to elements that are the same as those of the first embodiment.

A fluorescence signal detection apparatus 2 illustrated in FIG. 2 includes a sample cell 50 according to an embodiment of the present invention. The sample cell 50 is used in the optical signal detection method in the fluorescence signal detection apparatus 2. Further, the fluorescence signal detection apparatus 2 includes an excitation light irradiation optical system 20 that outputs excitation light $L_0$ to a predetermined area of the sample cell 50. Further, the fluorescence signal detection apparatus 2 includes a photo-detector 30 for detecting light Lf.

FIG. 3A is a plan view illustrating the sample cell 50, and FIG. 3B is a side-sectional view of the sample cell 50.

The sample cell 50 includes a base 51, a spacer 53, and an upper plate 54. The spacer 53 retains liquid sample S on the base 51 and forms a flow path 52 through which the liquid sample S flows. The upper plate 54 is made of glass plate and includes an injection opening 54a for injecting the liquid sample S and an air hole 54b for discharging the liquid sample S that has flowed through the flow path 52. Further, a membrane filter 55 is provided in a region between the injection opening 54a and the flow path 52. Further, a waste liquid reservoir 56 is formed at a region connected to the air hole 54b on the downstream side of the flow path 52. In the present embodiment, the flow path is formed by the spacer 53 on the upper side of the base 51, and the base 51 is formed by the dielectric plate 51. The base 51 also functions as a dielectric plate of the sensor chip portion. It is not necessary that the whole base is formed by the dielectric plate. The base may be formed in such a manner that only a part of the base, the part functioning as the sensor chip portion, is formed by the dielectric plate.

Further, a labeling secondary antibody adsorption area 57, a first measurement area 58, and a second measurement area 59 are sequentially formed on the base 51 of the sample cell 50 from the upstream side of the flow path 52. In the labeling secondary antibody adsorption area 57, photo-reactable labeling substance F has been physically adsorbed. The surface of the photo-reactable labeling substance F is modified with secondary antibody (second binding substance) $B_2$ that specifically binds to the antigen, which is the substance to be detected. In the first measurement area 58, a primary antibody (first binding substance) $B_1$ is immobilized. The primary antibody $B_1$ specifically binds to the antigen, which is the substance to be detected. In the second measurement area 59, a primary antibody $B_0$ is immobilized. The primary antibody $B_0$ does not bind to the antigen, which is the substance to be detected, but specifically binds to labeling secondary antibody $B_2$. The first measurement area 58 corresponds to a sensor portion and the second measurement area 59 corresponds to a reference portion. FIG. 2 illustrates the state of the sample cell 50 after the sample has been injected into the sample cell 50 and the antibody has bound to the labeling secondary antibody and flowed. Therefore, in FIG. 2, the labeling secondary antibody adsorption area 57 is not present anymore. In this example, a case in which two measurement areas, namely, the sensor portion and the reference portion, are provided in the sensor chip portion has been described. Alternatively, only the sensor portion may be provided.

In the first measurement area 58, a gold (Au) layer 58a, as a metal layer, is formed on the base 51. In the second measurement area 59, a gold (Au) layer 59a, as a metal layer, is formed on the base 51. Further, primary antibody $B_1$ is immobilized on the Au layer 58a of the first measurement area 58, and primary antibody $B_0$, which is different from the primary antibody $B_1$, is immobilized on the Au layer 59a of the second measurement area 59. The first measurement area 58 and the second measurement area 59 are structured in the same manner except that the immobilized primary antibodies differ from each other. The primary antibody $B_0$, which is immobilized in the second measurement area 59, does not bind to antigen A, but directly binds to secondary antibody $B_2$. Accordingly, it is possible to detect fluctuation factors related to reaction, such as the amount or activity of the labeling secondary antibody that has flowed through the flow path. Further, it is possible to detect fluctuation factors related to the degree of enhancement of surface plasmons, such as the excitation light irradiation optical system 20, the gold (Au) layer 58a, the gold (Au) layer 59a, and the liquid sample S. Further, the detected fluctuation factors can be used for calibration. It is not necessary that the primary antibody $B_0$ is immobilized in the second measurement area 59. Instead of the primary antibody $B_0$, a known amount of labeling substance may be immobilized in the second measurement area 59 in advance. The labeling substance may be the same kind of substance as the photo-reactable labeling substance the surface of which has be modified with the secondary antibody. Alternatively, the labeling substance may be a photo-reactable labeling substance that has a different wavelength and size from the photo-reactable labeling substance the surface of which has be modified with the secondary antibody. Further, the labeling substance may be a different photo-reactable labeling substance, such as a metal microparticle. In this case, detection of the fluctuation factors may be performed in such a manner to detect only the fluctuation factors related to the degree of enhancement of surface plasmons, such as the excitation light irradiation optical system 20, the gold (Au) layer 58a, the gold (Au) layer 59a, and the liquid sample S. Further, the detected fluctuation factors can be used for calibration. Whether the labeling secondary antibody $B_2$ or the known amount of labeling substance is immobilized in the second measurement area 59 may be appropriately determined based on the purpose and method of calibration.

The sample cell 50 can move in X direction relative to the excitation light irradiation optical system 20 and the photo-detector 30. After optical signal detection measurement is performed for the first measurement area 58, the second measurement area 59 is moved to an optical signal detection position, and optical signal detection is performed for the second measurement area 59.

The excitation light irradiation optical system 20 includes a light source 21, such as a semiconductor laser (LD), which outputs excitation light $L_0$. Further, the excitation-light irradiation optical system 20 includes a prism 22 arranged in such a manner that a surface of the prism 22 contacts with the dielectric plate 11. Further, the excitation light irradiation optical system 20 includes a light guide member including a lens 24 and a mirror 25. The light guide member condenses the excitation light $L_0$ output from the light source 21 and causes the condensed light to enter the prism 22 from a surface of the prism 22. Further, the excitation-light irradiation optical system 20 includes a driver 28 that drives the light source (semiconductor laser) 21.

The principle of the optical signal detection method (fluorescence detection method) using the optical signal detection apparatus 2, which is structured as described above, is similar to the principle of the optical signal detection method according to the first embodiment. In the present embodiment, the photo-reactable labeling substance similar to the one used in the first embodiment is used. Therefore, it is possible to achieve an advantageous effect similar to the first embodiment. Further, highly accurate measurement is possible by using a simple method.

Next, sensing using the optical signal detection apparatus 2 and the fluorescence detection method according to the second embodiment will be described.

With reference to FIG. 4, assay procedures will be described. In the assay procedures, blood (whole blood) is injected to the sample cell 50 from the injection opening, and an assay is performed. The blood is the assay target (examination target) as to whether an antigen, which is a substance to be detected, is included.

Step 1: Blood (whole blood) $S_0$, which is the assay target, is injected from the injection opening 54a. Here, a case in which the antigen that is the substance to be detected is included in the blood $S_0$ will be described. In FIG. 4, the blood (whole blood) $S_0$ is indicated by a mesh.

Step 2: The blood (whole blood) $S_0$ is filtered by the membrane filter 55, and large molecules, such as erythrocyte (red blood cells) and leukocyte (white blood cells), remain as a residue.

Step 3: Blood (plasma, blood plasma) S after blood cells (blood corpuscles) are removed by the membrane filter 55 penetrates into the flow path 52 by a capillary phenomenon. Alternatively, a pump may be connected to the air hole 54b to accelerate reaction, thereby reducing detection time. The pump sucks the blood after blood cells are removed by the membrane filter 55 and pumps (pressures to discharge) the sucked blood, thereby causing the blood to flow down through the path. In FIG. 4A, the blood (plasma, blood plasma) S is indicated by a shadow.

Step 4: The blood (plasma, blood plasma) S that has penetrated into the flow path 52 and the fluorescence labeling substance F that has been modified with the secondary antibody $B_2$ are mixed together. Accordingly, antigen A in the blood (plasma, blood plasma) S and the secondary antibody $B_2$ bind to each other.

Step 5: The blood (plasma, blood plasma) S gradually flows down to the air hole 54b side along the flow path 52. The antigen A that has bound to the secondary antibody $B_2$ binds to the primary antibody $B_1$ that has been immobilized in the first measurement area 58. Accordingly, a so-called sandwich is formed in which the antigen A is sandwiched between the primary antibody $B_1$ and the secondary antibody $B_2$.

Step 6: A part of the secondary antibody $B_2$ that has not bound to the antigen A binds to the primary antibody $B_0$ immobilized on the second measurement area 59. Further, even if the fluorescence labeling substance F modified with the secondary antibody that has bound neither to the antigen A nor to the primary antibody Bo remains in the measurement areas, the blood (plasma, blood plasma) S flowing so as to follow functions as washing liquid, and washes away floated substance and non-specifically-adsorbed substance.

As described above, in Steps 1 through 6, the blood is injected from the injection opening and a sandwich in which the antigen A is sandwiched between the primary antibody $B_1$ and the secondary antibody $B_2$ is formed in the measurement area 58. After Steps 1 through 6, the intensity of fluorescence from the first measurement area 58 is detected, thereby detecting the presence of the antigen and/or the concentration of the antigen. After then, the sample cell 50 is moved in X direction so that the fluorescence signal from the second measurement area 59 can be detected, and the fluorescence signal from the second measurement area 59 is detected. The fluorescence signal from the second measurement area 59 in which the primary antibody $B_0$ that binds to the secondary antibody $B_2$ is immobilized reflects reaction conditions, such as the amount of the secondary antibody that has flowed down and the activity of the secondary antibody. Therefore, if this signal is used as a reference (reference signal) and the signal from the measurement area is corrected based on the reference, it is possible to obtain a more accurate detection result. Further, even when a known amount of labeling substance (fluorescence substance and metal particle) is immobilized in advance in the second measurement area 59, as described above already, it is possible to use the fluorescence signal from the second measurement area 59 as a reference, and the signal from the first measurement area can be corrected based on the reference.

Figure 5A:
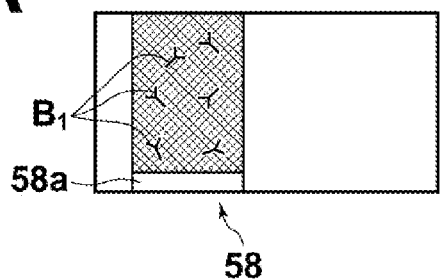
FIG. 5A is a diagram illustrating a method for immobilizing antibody $B_1$ on a metal layer (No. 1)
Figure 5B:
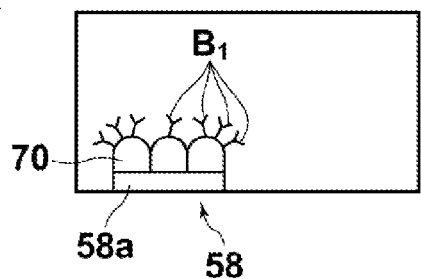
FIG. 5B is a diagram illustrating another method for immobilizing antibody $B_1$ on a metal layer (No. 2)

In FIGS. 2 through 4, the primary antibody $B_1$ that is immobilized in the measurement area 58 is two-dimensionally provided on a surface of the metal layer 59a. However, as illustrated in FIG. 5A, the primary antibody $B_1$ may be immobilized in a three-dimensionally-spread membrane region on the metal layer 58a. Alternatively, as illustrated in FIG. 5B, a structure 70 for increasing the surface area may be provided on the surface of the metal layer 58a, and the antibody $B_1$ may be three-dimensionally immobilized on the structure 70.

The structure 70 may be made of any kind of light transmissive substance, such as polystyrene and glass. It is desirable that the refractive index is low and the size (thickness) of the structure is small to prevent disturbance of the surface plasmons, as described later. The structure 70 may be formed by a thin coating by using a vapor deposition method, a sputtering method, a spin-coat method or the like. Then, the surface of the thin coating may be randomly coarsened or roughened by plasma processing or solvent processing. Alternatively, polystyrene microparticles that have diameters of approximately 10 to 500 nm may be immobilized on the surface of the gold film by physical adsorption or by chemical bond.

When the assay described in the second embodiment is performed, the motion of the photo-reactable labeling substance in the flow path is dominated by diffusion. In the assay described in the second embodiment, fluorescence labeling substance, which is the photo-reactable labeling substance, is immobilized (at a sensor portion) on the inner wall of the flow path (micro-flow path) through the antigen or the antibody. Since the diffusion time of the photo-reactable labeling substance remarkably differs according to the particle diameter of the photo-reactable labeling substance, the range of particle diameter appropriate for the photo-reactable labeling substance is obtained as described below. In the following description, it is assumed that the photo-reactable labeling substance has spherical form to obtain the range of the particle diameters.

Diffusion time $\tau$ of the photo-reactable labeling substance is represented by Formula (1):

$$\tau h^2/D \qquad (1).$$

Here, h: diffusion distance and D: diffusion constant.

When Einstein-Stokes formula (2) is used, the diffusion constant D can be obtained from hydrodynamic radius d of the photo-reactable labeling substance. Therefore, the diffusion time $\tau$ that is necessary for the photo-reactable labeling substance to diffuse to the primary antibody by distance (diffusion distance) h is obtained, the diffusion to the primary antibody being necessary for formation of the sandwich. When the sandwich is formed on a two-dimensional flat surface (inner wall) of the flow path, the diffusion distance h represents the height of the flow path. When the sandwich is formed in a three-dimensional structure, such as the membrane, the diffusion distance h represents a distance to the primary antibody that is immobilized on the three-dimensional structure.

$$D = K_B T / 3 \pi \eta d \qquad (2).$$

Here, $K_B$: Boltzmann constant, T: absolute temperature, $\eta$: viscosity of solvent, and d: hydrodynamic radius.

Figure 6:
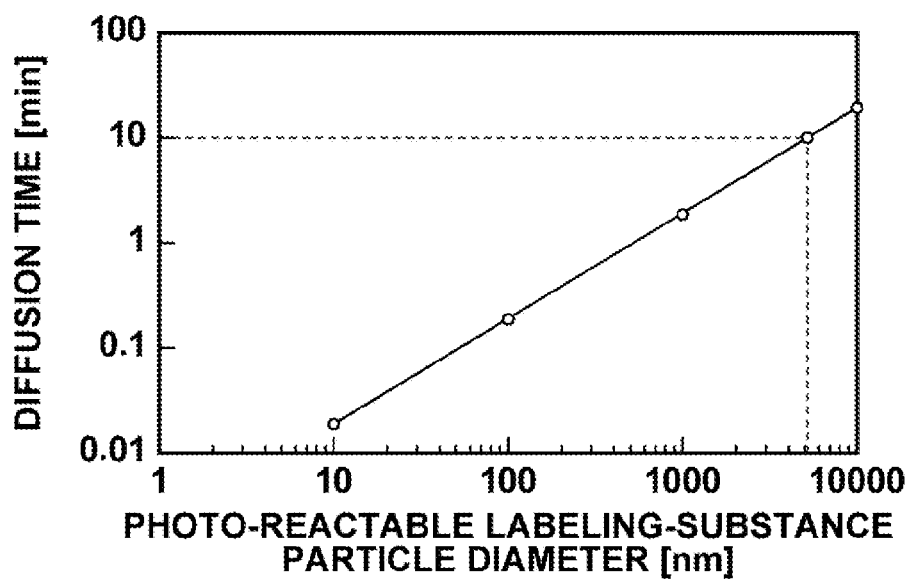
FIG. 6 is a graph showing diffusion time with respect to the particle diameter of a photo-reactable labeling-substance.

FIG. 6 is a graph showing time required for diffusion of the photo-reactable labeling substance by a distance h of 30 μm to the primary antibody with respect to the particle diameter φ of the photo-reactable labeling-substance. In FIG. 6, the distance h, which is a distance to the primary antibody that is necessary to form the sandwich, is assumed to be 30 μm. Generally, time for assay that is practically applicable to diagnosis (diagnosis level) is less than or equal to 10 minutes. FIG. 6 shows that it is effective that the particle diameter of the photo-reactable labeling substance is less than or equal to φ5300 nm to realize the assay time that is less than or equal to 10 minutes in the micro-flow-path that has a height of 30 μm. Therefore, when reaction occurs in the micro-flow-path, it is desirable that the particle diameter of the photo-reactable labeling substance is less than or equal to φ5300 nm.

Further, when an optical signal is detected utilizing the electric field enhancement effect by surface plasmon excitation, it is necessary to consider the disturbance of the surface plasmons by the photo-reactable labeling substance.

Figure 7A:
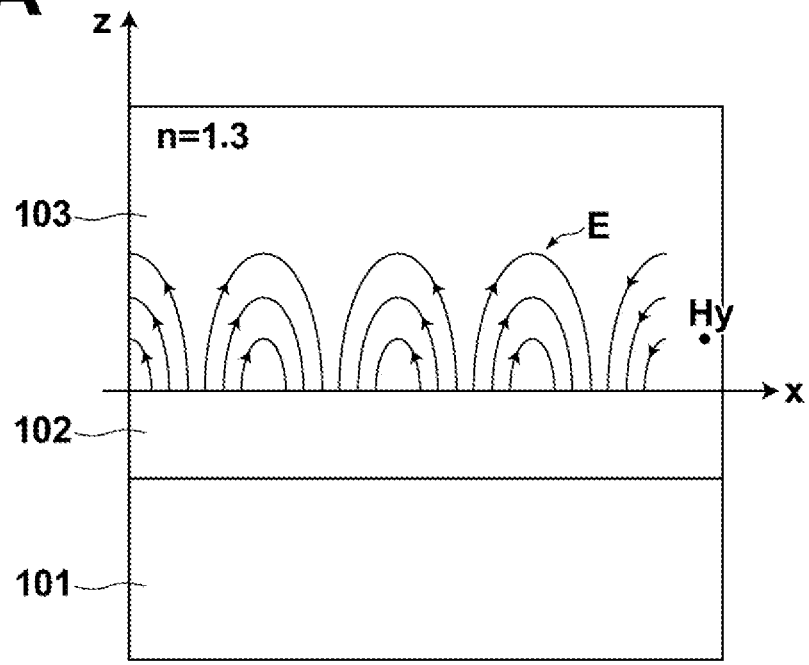
FIG. 7A is a schematic diagram illustrating electric field E when an aqueous-solvent layer is present on a metal layer
Figure 7B:
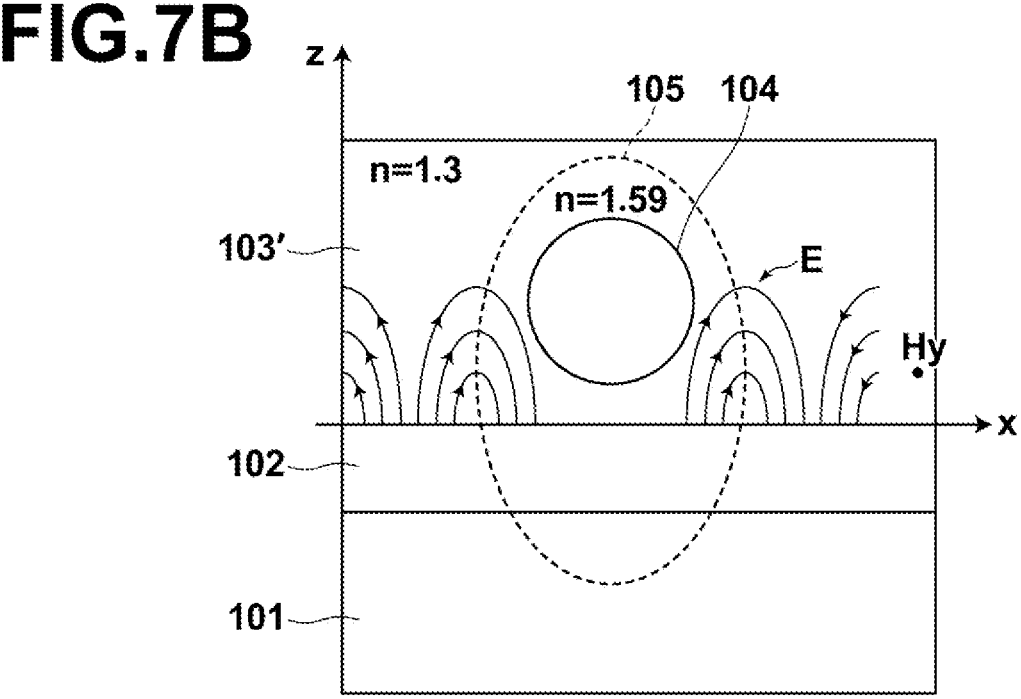
FIG. 7B is a schematic diagram illustrating electric field E when a photo-reactable labeling-substance is present on a metal layer.

As described already, as the light transmissive material for the photo-reactable labeling substance, polystyrene, glass or the like, which has higher refractive index than aqueous solvent, is used. For example, the refractive index n of polystyrene is 1.59 to 1.6. When the photo-reactable labeling substance that has a high refractive index as described above is placed in the vicinity of the metal layer, generation of surface plasmons may be suppressed or disturbed. This phenomenon is considered by multiple layer approximation in which the flow path is divided into three layers of a prism layer 101, a metal layer 102, and a solvent layer 103. FIG. 7A is a schematic diagram illustrating electric field E generated on the surface of the metal layer when an optical beam enters the metal layer from the prism layer 101 side. In FIG. 7A, only an aqueous-solvent layer is present on the metal layer 102. FIG. 7B is a schematic diagram illustrating electric field E generated on the surface of the metal layer when an optical beam enters the metal layer from the prism layer 101 side. In FIG. 7B, a photo-reactable labeling-substance 104 that is polystyrene is present on the metal layer 102.

Figure 8:
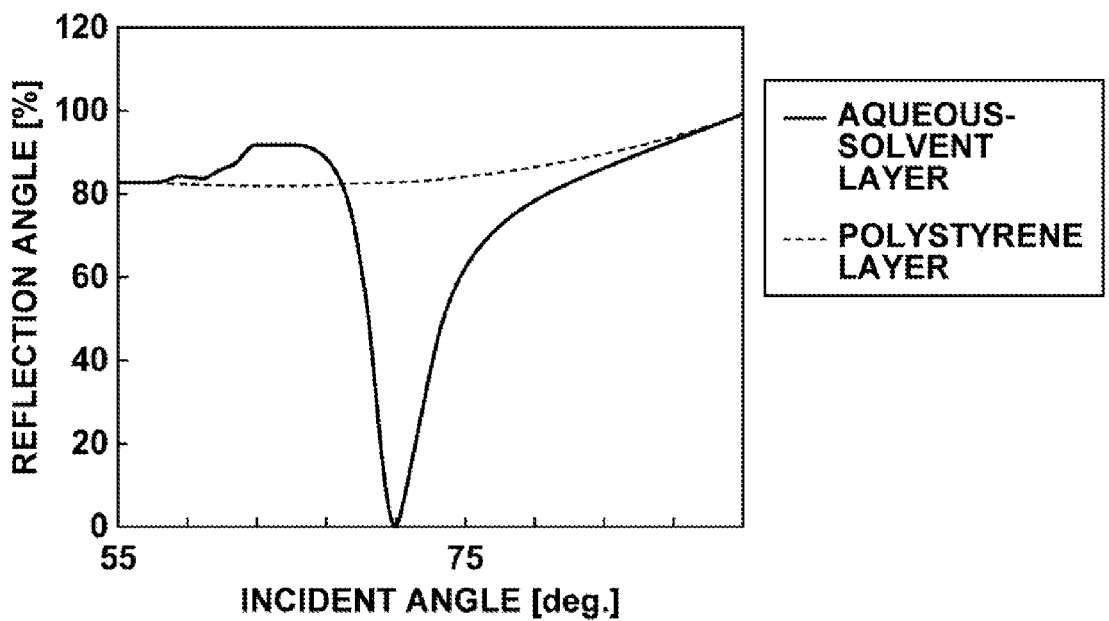
FIG. 8 is a graph showing relationships between incident angles and reflectance in the cases illustrated in FIGS. 7A and 7B.

If the thicknesses of the prism layer and the solvent layer 103 (103') are sufficiently thick, and the refractive index of the prism layer 101 and the refractive index and the thickness of the metal layer 102 are already determined, the condition of plasmons excited on the surface of the metal layer is determined by the refractive index of the solvent on the metal layer. FIG. 8 is a graph showing relationships between incident angles of the excitation light that enters the interface and reflectance. FIG. 8 illustrates a case in which only the aqueous solvent layer is present on the metal layer 102 (indicated by a solid line) and a case in which a polystyrene layer is present on the metal layer (indicated by a broken line). This graph shows that when the aqueous solvent layer (refractive index n=1.33) is present on the solvent side, a resonance angle at which surface plasmons are generated is present, but when the polystyrene layer (refractive index n=1.59) is present, surface plasmons are not generated (resonance angle is not present). In other words, as illustrated in FIG. 7B, the electric field in a region 105 indicated by a dot line in FIG. 7B is disturbed by the photo-reactable labeling substance 104. This shows that when an assay is performed by using a photo-reactable labeling substance that has a high refractive index (polystyrene or glass) and the photo-reactable labeling substance is immobilized in the vicinity of the metal layer, surface plasmons are suppressed and reduced. Therefore, it becomes impossible to enhance the electric field.

Figure 9:
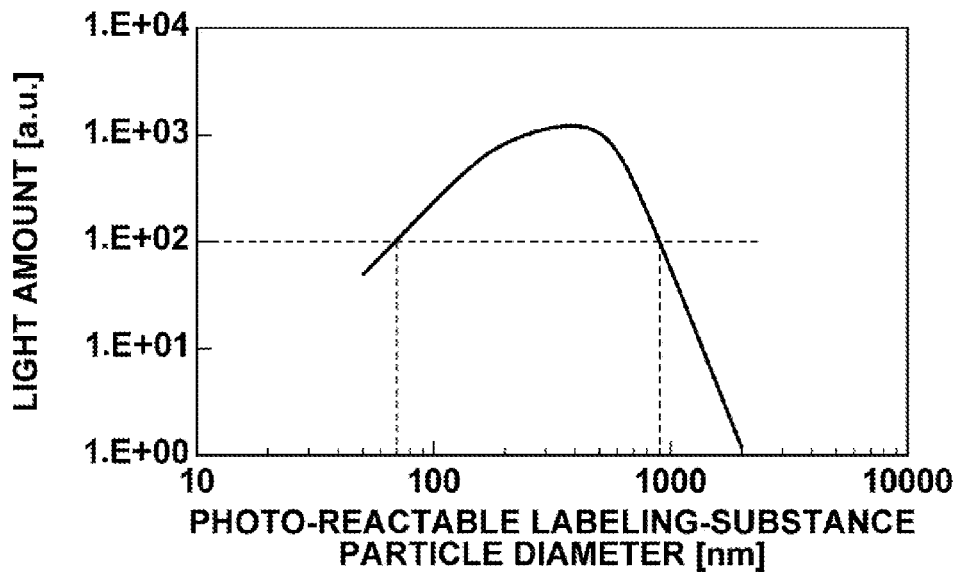
FIG. 9 is a simulation diagram showing a relationship between the particle diameter of the photo-reactable labeling-substance and a fluorescence amount.

The disturbance of surface plasmons by the photo-reactable labeling substance as described above has been considered, and a relationship between the particle diameter of the photo-reactable labeling-substance and a light amount from the labeling substance has been simulated. FIG. 9 shows the result of the simulation. The amount of the photo-reactable substance that is included in a particle increases as the particle diameter increases. Therefore, the light amount increases as the particle diameter increase until the particle diameter reaches 400 nm. However, when the particle diameter exceeds 500 nm, the light amount sharply decreases. That is because when the particle diameter exceeds 500 nm, the disturbance of surface plasmons by the photo-reactable labeling substance increases. An increase in the light amount caused by an increase in the diameter of the photo-reactable labeling substance and the disturbance of surface plasmons by the photo-reactable labeling substance are considered with reference to FIG. 9. FIG. 9 shows that it is desirable that the particle diameter of the photo-reactable labeling substance is in the range of 70 nm to 900 nm to prevent the light amount from dropping by more than a digit or the like from the peak amount when the particle diameter is 300 nm.

Further, a more desirable particle diameter range for the photo-reactable labeling substance that is a fluorescence labeling substance has been found as described below. The desirable particle diameter range has been found from the view point of the optical signal intensity distribution of the photo-reactable substance and the flow path immune reaction. In the following description, a fluorescence labeling substance including a fluorescent dye molecule as a photo-reactable substance is used, and a gold layer is used as the metal layer and considered. However, a similar tendency is observed for a different photo-reactable substance that generates fluorescence, other than the fluorescent dye molecule, and only the absolute value of the result differs from the result of the fluorescent dye molecule. Therefore, the particle diameter range is applicable to such different photo-reactable substance.

Figure 10:
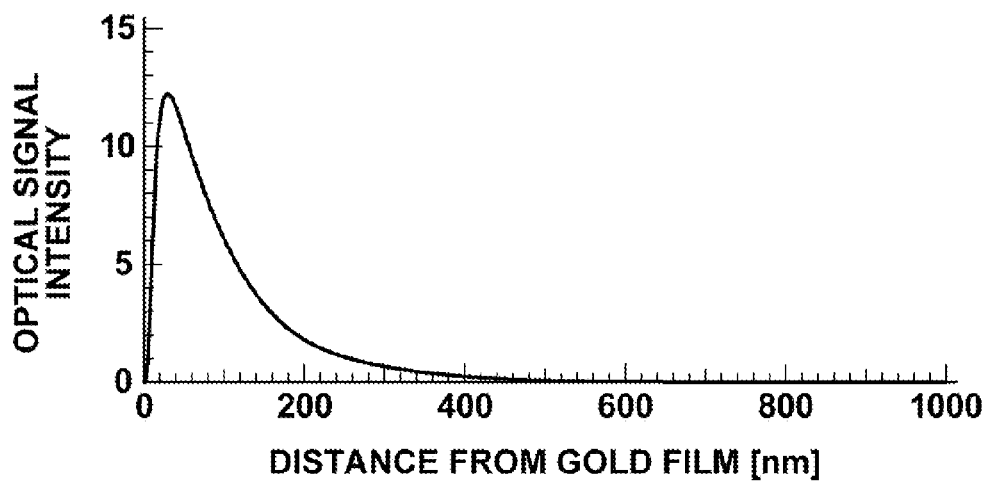
FIG. 10 is a simulation diagram showing a distance-dependent characteristic of the intensity of an optical signal output from the photo-reactable labeling-substance, the distance from the metal layer.

FIG. 10 is a simulation diagram showing a distance-dependent characteristic of the intensity of an optical signal output from an excited photo-reactable labeling-substance, the distance from the metal layer. In FIG. 10, a fluorescent dye molecule is used as the photo-reactable substance, and a gold layer is used as the metal layer. The optical signal from the photo-reactable labeling substance becomes zero in the extremely-close vicinity of the metal layer because metal quenching occurs. However, the optical signal sharply increases until the distance from the metal layer reaches approximately 30 nm. After 30 nm, as the distance increases, the optical signal exponentially attenuates. As described above, the distribution of the intensity of the optical signal is very complex. Therefore, it is important to control the diameter of a bead (particle).

Figure 11:
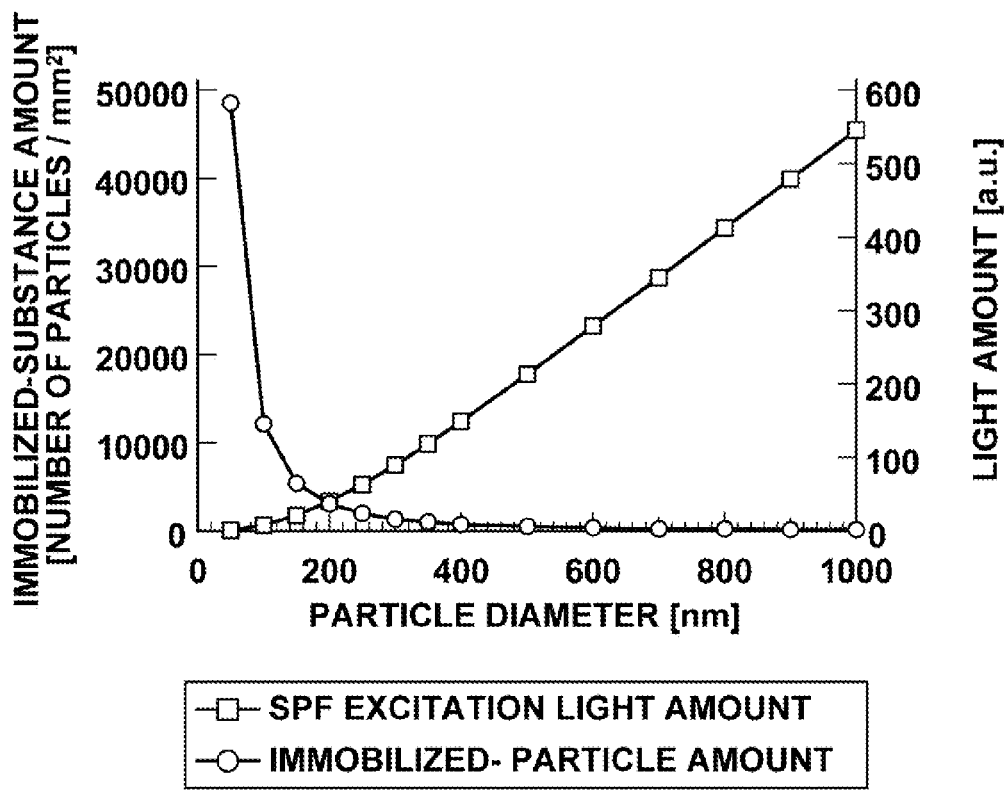
FIG. 11 is a simulation diagram showing a particle-diameter-dependent characteristic of a light amount and a particle-diameter-dependent characteristic of an amount of immobilized substance.

FIG. 11 is a diagram obtained by simulating a particle-diameter-dependent characteristic of a light amount and a particle-diameter-dependent characteristic of an amount of immobilized substance.

In FIG. 11, the right vertical axis represents a light amount generated from a whole particle of a photo-reactable labeling substance when the photo-reactable labeling substance is irradiated with excitation light while the photo-reactable labeling substance is directly in contact with the surface of the metal layer on the prism. A sufficient number of fluorescent dye molecules are evenly enclosed (encapsulated) in the photo-reactable labeling substance. Further, supposing that the quantum yield is 1 for the case of fluorescence, the distance from the prism surface and the volume of the particles that are present within the distance are multiplied together, and the integral of the product is obtained with respect to the length of the particle diameter. As FIG. 11 shows, as the particle diameter increases, the light amount from the labeling substance increases. That is because as the particle diameter increases, the fluorescent dye in a region that is away from the surface of the metal layer, and in which the intensity of the excitation light becomes weak, increases, however, the fluorescent dye in a region that is located close to the metal layer, and in which the intensity of the light is strong, increases. Consequently, the light amount generated from the whole labeling substance increases.

Next, an optimum particle diameter from the view point of the flow path immune reaction has been calculated. In immune reaction, the adsorption formula of Langmuir and a diffusion formula were used. Further, the flow speed in the flow path and steric hindrance of the particle are considered to perform simulation. Here, from the viewpoint of realistic cost, it is assumed that even if the particle diameter changes, the particle has the same weight %, and the total amount of the immune reaction substance with which the surfaces of all of the particles are modified is the same. In FIG. 11, the left vertical axis represents the immobilized amount of the photo-reactable labeling substance when hCG sandwich assay has been conducted. In FIG. 11, hCG antigen concentration is 10 pM. As FIG. 11 shows, the immobilized amount of the substance (immobilized-substance amount) is represented by the number of particles in a unit area. As the diameter of the particle increases, the immobilized amount of the substance increases.

Figure 12:
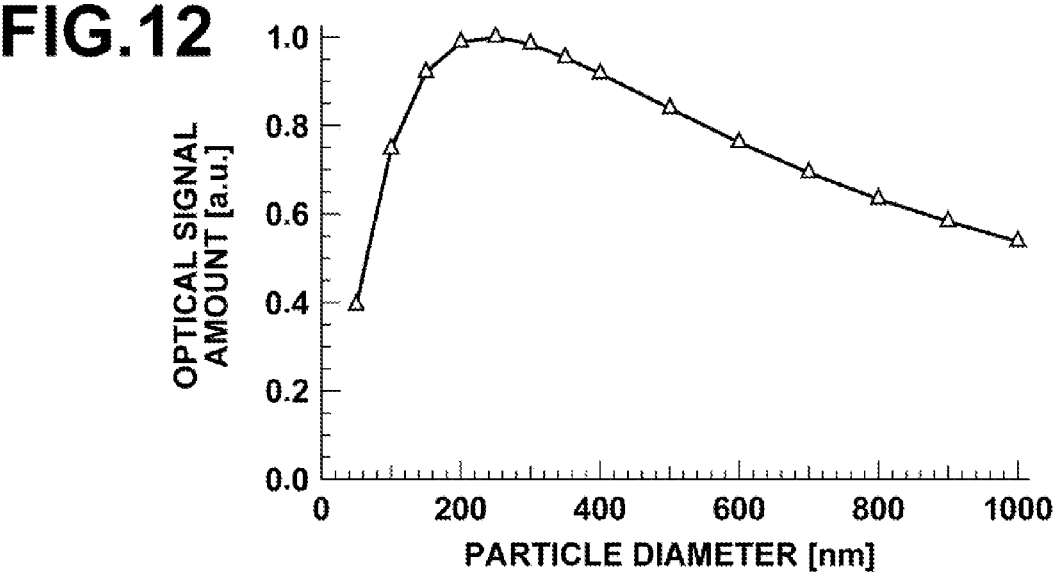
FIG. 12 is a diagram illustrating a particle-diameter-dependent characteristic of a total light amount from a photo-reactable labeling-substance immobilized in an area of 1 mm$^2$.

When the aforementioned two factors (the light amount from a molecule of labeling substance and the immobilized-substance amount of labeling substance) are combined, it is possible to obtain the light amount from the labeling substance immobilized in a unit area of 1 mm². FIG. 12 is a diagram illustrating a particle-diameter-dependent characteristic of a total light amount from a labeling-substance immobilized in an area of 1 mm². In FIG. 12, the product of the immobilized amount and the light amount has been obtained. In FIG. 12, the vertical axis represents a signal value obtained by normalizing the total light amount by the maximum value.

FIG. 12 shows that when the light amount is 70% or higher, the particle diameter in the range of 90 nm to 700 nm is effective.

Here, the reason why the light amount is 70% or higher is as follows.

Figure 13:
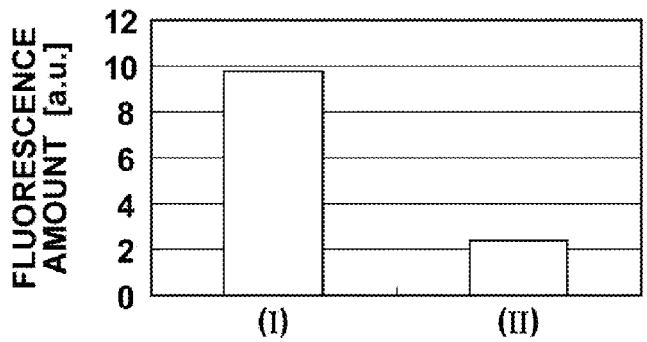
FIG. 13 is a diagram illustrating a result of measurement of fluorescence amounts by an SPF method and by an epifluorescence method.

When the same fluorescence labeling substance (fluorescence labeling substance having the same performance) is used in a fluorescence detection method by surface plasmon excitation (hereinafter, referred to as "SPF method") and in a fluorescence detection method by epifluorescent excitation (hereinafter, referred to as "epifluorescent method"), the degree of signal enhancement of the SPF method is approximately ten times higher than that of the epifluorescent method. Therefore, the SPF method can perform high-sensitivity measurement. When a gold layer is used in the SPF method, plasmons are excited. Therefore, it is necessary to set the excitation wavelength to 600 nm or longer. Meanwhile, generally, the fluorescence labeling substance has higher fluorescence amount as the fluorescence wavelength is shorter, and such fluorescence labeling substance has higher performance. In other words, in the epifluorescent method, it is possible to use a fluorescence labeling substance that has high performance, but in the SPF method, it is necessary to use a fluorescence labeling substance that has long wavelength, and which has low performance. As typical values of output fluorescence, FIG. 13 shows values obtained by measurement using a fluorescence spectrophotometer (No. F-7000, manufactured by Hitachi, Ltd.). In the measurement, an aqueous-solvent dilution of the following particles that have substantially the same particle diameters and manufactured by Invitrogen Corporation are measured: fluorescence microparticle (I) (No. F8810, diameter 0.2 um, excitation wavelength 580 nm, fluorescence wavelength 605 nm, and manufactured by Invitrogen Corporation); and fluorescence microparticle (II) (No. F8807, diameter 0.2 um, excitation wavelength 660 nm, fluorescence wavelength 680 nm, and manufactured by Invitrogen Corporation). As FIG. 13 shows, the light amount of the fluorescence microparticle (I) that has the fluorescence wavelength of 605 nm is approximately 4.4 times higher than that of the fluorescence microparticle (II). Further, the performance of the fluorescence microparticle (I) is higher than that of the fluorescence microparticle (II). In the SPF method, it is necessary to use excitation wavelength that is 600 nm or greater, and the fluorescence microparticle (II) is used. In contrast, in the epifluorescent method, the excitation wavelength is not limited. Therefore, it is possible to use the fluorescence microparticle (I). As described above, since a fluorescence labeling substance that has different performance is used, the magnitude of the advantage of the SPF method over the epifluorescent method decreases from the advantage achieved when the same fluorescence labeling substance is used in both of the methods.

Specifically, when the SPF method and the fluorescence microparticle (II) are combined, the effect is 10 ((SPF enhancement degree: 10)×(light amount of the fluorescence microparticle (II): 1)=10). Meanwhile, when the epifluorescent method and the fluorescence microparticle (I) are combined, the effect is 4.4 ((enhancement degree: 1)×(light amount of the fluorescence microparticle (I): 1)=4.4). In this case, the ratio of the signal enhancement effect of the SPF method relative to that of the epifluorescent method is 10/4.4=2.3 including the difference in the performance of the fluorescence microparticles. As described above, when the performance of the fluorescence microparticles that can be used in each of the methods is included (considered), the signal enhancement effect of the SPF method decreases from the signal enhancement effect when the fluorescence microparticles that have the same performance are used in the two methods.

In FIG. 12, the maximum value of the optical signal amount is a value at which the enhancement degree of the SPF method is approximately 10 times higher than that of the epifluorescent method. Therefore, in FIG. 12, when the optical signal amount is not the maximum value, the enhancement degree per se decreases. It is desirable that the signal enhancement effect by the SPF method is at least approximately 1.6 times higher than that of the epifluorescent method. If (enhancement degree A)/(fluorescence performance difference: 4.4)>1.6, (enhancement degree A)>1.6×

4.4~7.0. Therefore, if the enhancement degree A of the SPF method is 7 times or higher, in other words, if the value is 70% or higher than the maximum value in FIG. 12, it is possible to obtain fluorescence signal amount that is at least 1.6 times higher than that of the epifluorescent method.

Further, from the view point of the quantitative characteristic of measurement, it is considered that a CV (coefficient of variation) value that functions as an index for statistic dispersion based on the immobilized amount should be kept less than or equal to a certain value. From this view point, a desirable particle diameter is considered. According to the statistic theory, obtained signals at time of immobilized amount N is influenced by the statistic dispersion (shot noise) of √N. At this time, the labeling-substance-number dependency of the CV value √N/N=1/√N % is as illustrated in FIG. 14.

Figure 14:
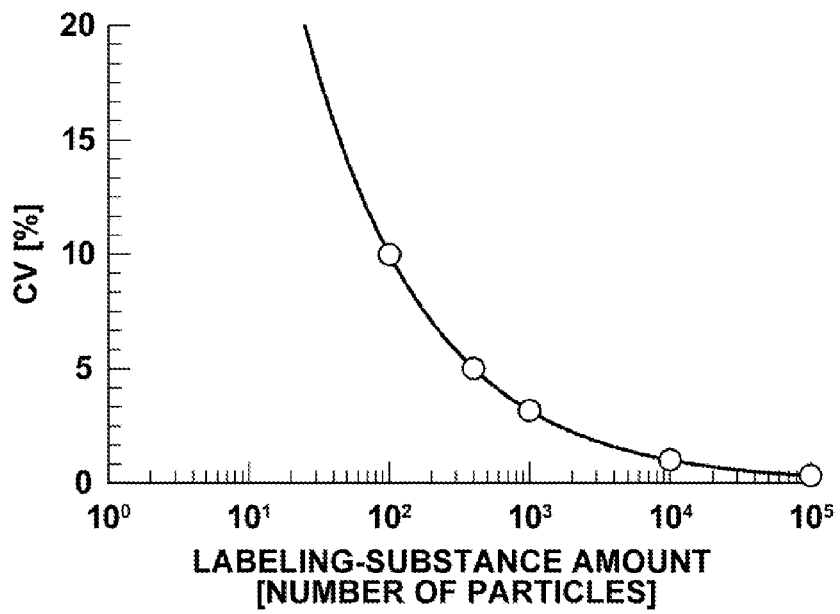
FIG. 14 is a diagram illustrating a labeling-substance-particle-number-dependent characteristic of a CV value.

As FIG. 14 shows, it is necessary that the immobilized amount is 400 particles or higher to control the statistic dispersion by the number of particles of the labeling substance at CV=5% or less. If the value needs to be reduced to CV=3% or less, it is necessary that the immobilized amount is 1111 particles or more.

When the immobilized area is 1 mm$^2$, if CV=5%, 400 particles/mm$^2$ and if CV=3%, 1111 particles/mm$^2$. Therefore, when the hCG antigen concentration is 10 pM, if the aforementioned CV values are tried to be achieved, it is possible to obtain the range of particle diameters based on the immobilized amount illustrated in FIG. 11. When CV=5%, the particle diameter is less than or equal to 559 nm, and when CV=3%, the particle diameter is less than or equal to 333 nm. The static dispersion is lower as the number of particles of the labeling substance is higher, in other words, the static dispersion is lower as the particle diameter is smaller.

As described above, the particle diameter that can maintain the advantage over the epifluorescent method and that can make the CV value achieve the quantitative characteristic less than or equal to the following values is in the range of 90 to 558 nm to achieve CV=5% or less and in the range of 90 to 338 nm to achieve CV=3% or less.

The aforementioned desirable particle diameter ranges determined from the view point of the statistic dispersion, specifically, when the CV is 5%, the particle diameter should be less than or equal to 558 nm, and optionally when the CV is 3%, the particle diameter should be less than or equal to 333 nm may be similarly applied to a case in which the photo-reactable substance does not generate fluorescence.

Further, for the case of performing an assay on a two-dimensional plane, which is a simple method, by omitting the process of forming a three-dimensional structure for immobilizing the primary antibody in the flow path, the range of desirable particle diameters of the photo-reactable labeling substance is obtained as described below. Here, as the photo-reactable labeling substance, fluorescence labeling substance including a fluorescent dye molecule is used. However, the obtained range of particle diameters can be similarly applicable to a case in which a different photo-reactable substance generating fluorescence is used.

It is generally considered that for the purpose of general diagnosis, the antigen concentration of detection limit of approximately 1 pM (picomolar: ×10$^{-12}$ mol/l) is necessary. Therefore, a desirable particle diameter of the fluorescence labeling substance is obtained by setting, as a target value, the sensitivity characteristic that can detect the antigen concentration of 1 pM or less and a two-digit dynamic range, in other words, concentration of up to 100 pM.

Figure 15:
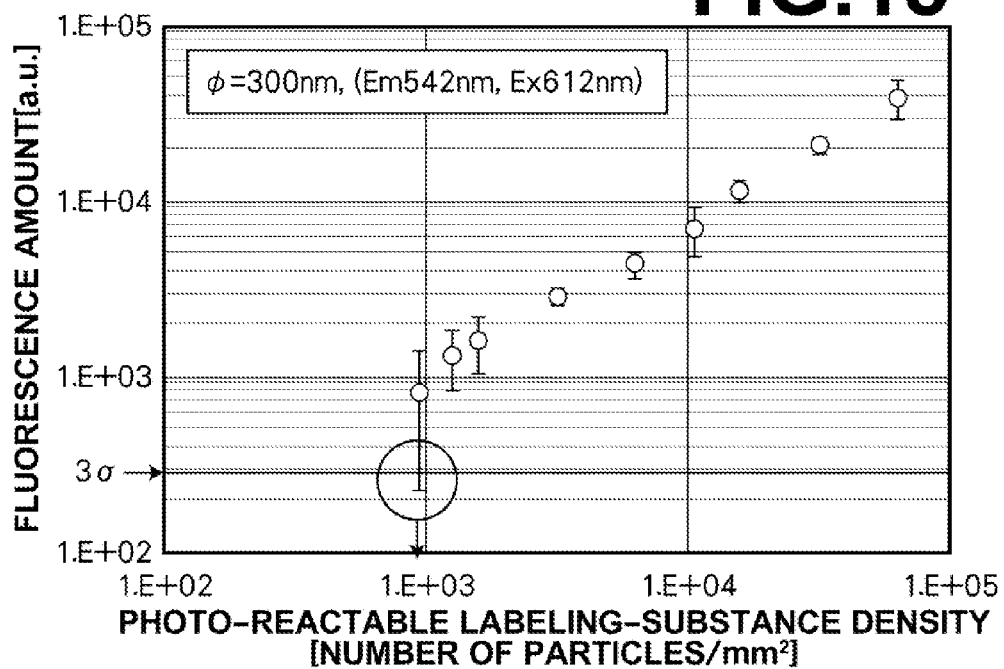
FIG. 15 is a diagram illustrating calibration curve data of fluorescence-labeling substance.

For a sample that has an antigen concentration of 1 pM, the conditions of an assay are set as follows: the diameter of a detection area is 1 mm (the area of the detection area is 3.1 mm$^2$); the total amount of the sample that flows down the flow path is 30 µl (this amount is a standard value in a general simple blood diagnosis apparatus as an amount after pre-processing before injection to the flow path and as an amount after blood cells are separated by a membrane filter); and the antigen capture ratio is 0.2% (Generally, the antigen capture ratio is approximately 0.2% to 2%. Therefore, the ratio is set at 0.2% so that detection is possible even if the ratio is at the lowest level). When the conditions are set as described above, antigens of 1.2×10$^4$ molecules (pieces)/mm$^2$ should be immobilized in the detection area to perform detection. Here, the value of 1.2×10$^4$ molecule/mm$^2$ is a target immobilized amount. Meanwhile, FIG. 15 shows calibration curve data of fluorescence labeling substance (diameter 300 nm, excitation wavelength 542 nm, and fluorescence wavelength 612 nm) that has been produced by the aforementioned procedures. The fluorescence labeling substance has been produced by using an epifluorescent detection apparatus (LAS-4000, epifluorescent type, manufactured by FUJIFILM Corporation). FIG. 15 shows a result obtained by using excitation light of green LED (light-emitting diode) that has a center wavelength of 520 nm and by detecting fluorescence through a filter for green fluorescence. At this time, the detection limit density was 1.0×10$^3$ particles/mm$^2$, at which an error bar intersects with the background value of the fluorescence detection apparatus of 3δ (δ is a standard deviation).

This result shows that when fluorescence labeling substance of φ300 nm is used, detection is possible at an immobilized amount that is 1/12 of the target immobilized amount (1.2×10$^4$ molecules/mm$^2$), and that the sensitivity of detection can be increased so that antigen detection is possible at an antigen concentration of 1 pM or less. Further, this result shows that even if the particle diameter of the fluorescence labeling substance is less than 300 nm, detection is possible with respect to a sample of 1 pM. Further, when fluorescent dye molecules are included at the same density, the fluorescence amount output from a particle of the fluorescence labeling substance is proportional to the cube of the radius of the fluorescence labeling substance (r$^3$). Therefore, when a fluorescence labeling substance of φ130 nm is used, the fluorescent amount for one particle is 1/12 of the fluorescent amount when a fluorescence labeling substance of φ300 nm is used. However, detection at the antigen concentration of 1 pM is still possible. Therefore, the minimum value of the particle diameter of the fluorescence labeling substance for performing detection at the antigen concentration of 1 pM is set approximately at φ130 nm. Here, it is assumed that the fluorescent dye molecule density in the fluorescent labeling substance is substantially constant.

Meanwhile, when the particle diameter of the fluorescence labeling substance is increased, the amount of the enclosed fluorescent dye molecules increases. Therefore, the fluorescence signal amount increases, and that is advantageous to the detection light amount. However, the number of particles of fluorescence labeling substance that can be immobilized in a certain area on a two-dimensional plane (immobilized amount) is limited due to steric hindrance. When the dynamic range is a two-digit number and the detection upper limit concentration is 100 pM, the immobilized amount is 1.2×10$^6$ particles/mm$^2$. At this time, when a particle of fluorescence labeling substance binds to a molecule of an antigen, the size of the particle that can most densely fill the space is φ500 nm. Therefore, the upper limit of the size of the fluorescence labeling substance that can achieve the target immobilized amount is φ500 nm.

As described above, a more desirable particle diameter of the fluorescence labeling substance is 130 nm to 500 nm.

In the above description, the desirable range of particle diameters was obtained assuming that the photo-reactable labeling substance has spherical form. However, it is not necessary that the photo-reactable labeling substance has spherical form. When the photo-reactable labeling substance does not have spherical form, the particle may be approximated to spherical form by using an average length of the maximum width and the minimum width of the particle as the particle diameter.

<Embodiment 3>

Figure 16A:
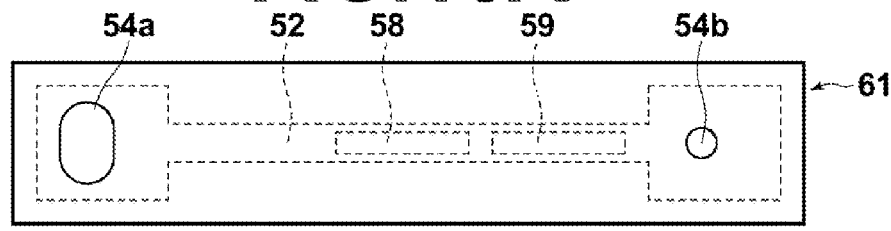
FIG. 16A is a plan view illustrating a sample cell in a kit for detecting an optical signal that is used in an optical signal detection method according to a third embodiment of the present invention.
Figure 16B:
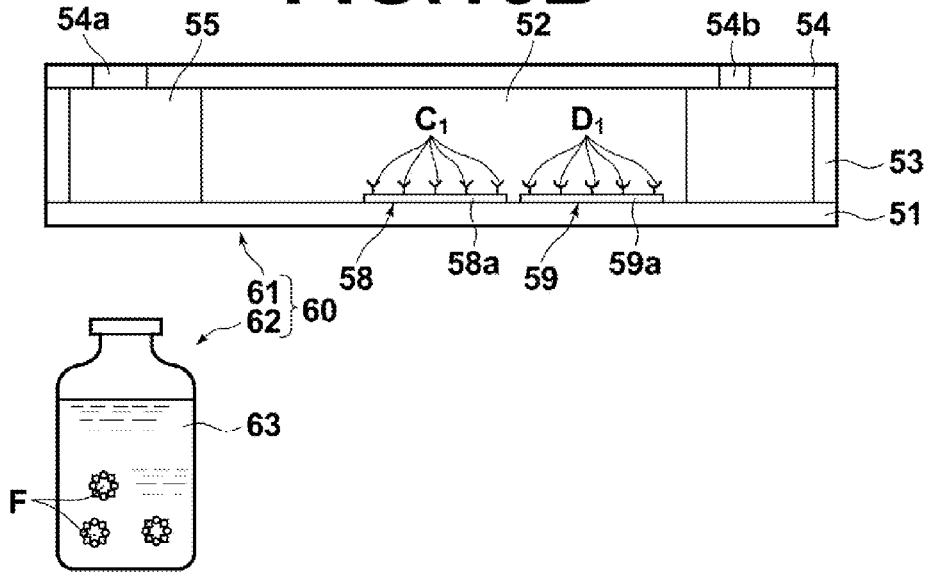
FIG. 16B is a diagram showing a side-sectional view of the sample cell illustrated in FIG. 16A and a solution for labeling.
Figure 17:
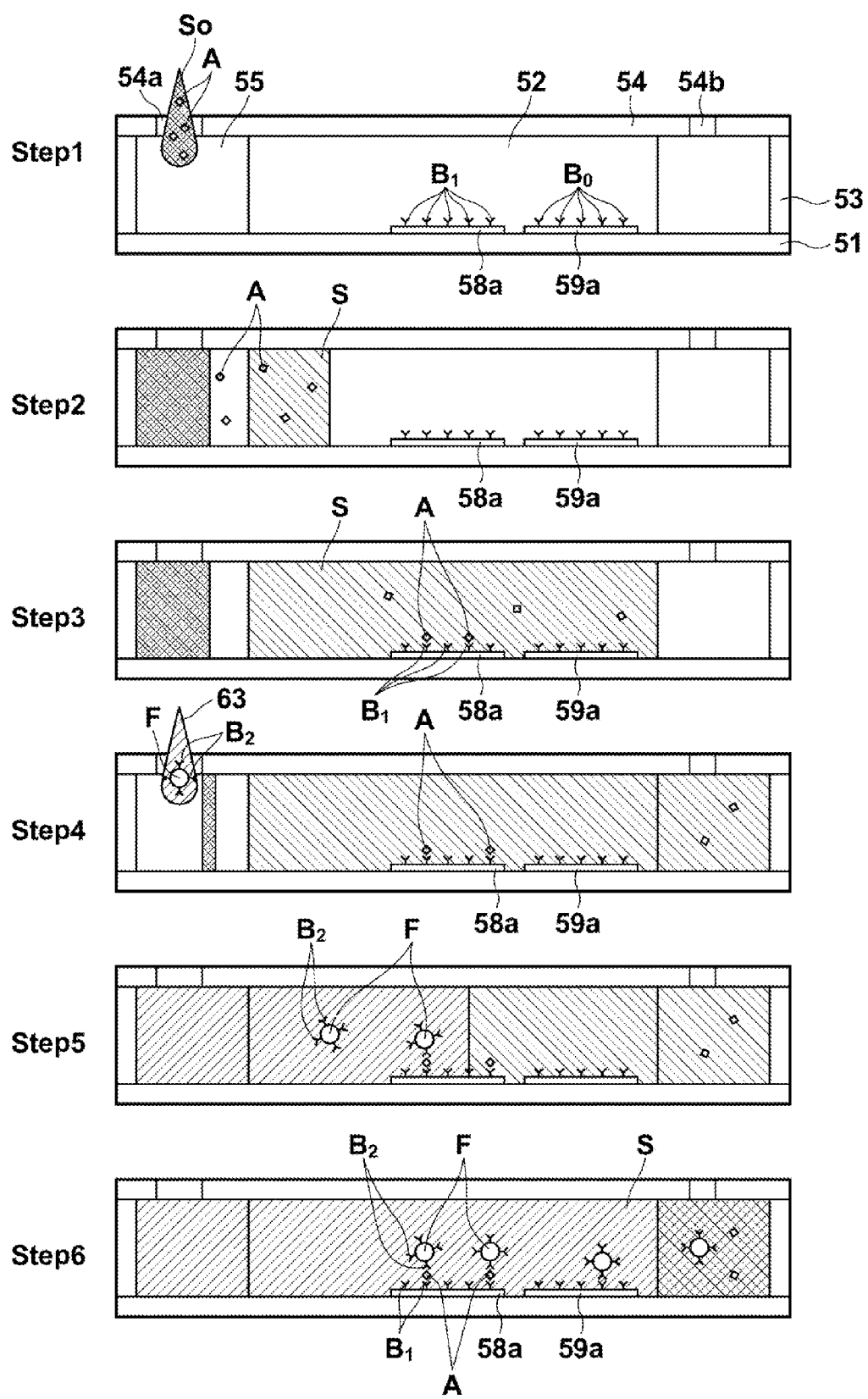
FIG. 17 a diagram illustrating procedures of an assay when a kit for detecting an optical signal is used.

An optical signal detection method according to a third embodiment will be described with reference to FIGS. 16A, 16B and 17. The optical signal detection method according to the third embodiment uses a kit for detecting an optical signal according to an embodiment of the present invention. In FIGS. 16A, 16B and 17, the same reference numerals are used for the elements as those of the aforementioned sample cell, and detailed descriptions of these elements are omitted.

FIG. 16A is a plan view illustrating a sample cell 61 in a kit 60 for detecting an optical signal. FIG. 16B is a diagram showing a side-sectional view of the sample cell and an ampule 62 containing a solution for labeling.

The kit 60 for detecting an optical signal includes the sample cell 61 and a solution 63 for labeling, which is injected into the flow path of the sample cell 61 together with the liquid sample or after the liquid sample flows down. The solution 63 for labeling contains photo-reactable labeling substance F modified with the secondary antibody $B_2$, as the second binding substance, which specifically binds to the antigen A.

The sample cell 61 differs from the sample cell 50 in the second embodiment only in that a physical adsorption area in which photo-reactable labeling substance that has been modified with the secondary antibody is physically adsorbed is not provided in the sample cell 61. The remaining structure of the sample cell 61 is substantially the same as that of the sample cell 50 in the second embodiment.

As the optical signal detection apparatus, the apparatus of the second embodiment illustrated in FIG. 2 can be used. When the kit 60 for detecting an optical signal of the present embodiment is used, the substance to be detected is labeled with the photo-reactable labeling substance in a manner similar to the second embodiment. Therefore, it is possible to perform highly accurate measurement similar to the second embodiment.

Further, sensing by the optical signal detection apparatus 2 when the kit 60 for detecting the optical signal is used will be described.

With reference to FIG. 17, assay procedures will be described. In the assay procedures, blood (whole blood) is injected into the sample cell 61 from the injection opening, and an assay is performed. The blood is the assay target (examination target) as to whether an antigen, which is a substance to be detected, is included.

Step 1: Blood (whole blood) $S_0$, which is the assay target, is injected from an injection opening 54a. Here, a case in which the antigen that is the substance to be detected is included in the blood $S_0$ will be described. In FIG. 17, the blood (whole blood) $S_0$ is indicated by a mesh.

Step 2: The blood (whole blood) $S_0$ is filtered by the membrane filter 55, and large molecules, such as erythrocyte (red blood cells) and leukocyte (white blood cells) remain as a residue. Then, the blood (plasma, blood plasma) S after blood cells (blood corpuscles) are removed by the membrane filter 55 penetrates into the flow path 52 by a capillary phenomenon. Alternatively, a pump may be connected to the air hole to accelerate reaction, thereby reducing detection time. The pump sucks the blood after blood cells (blood corpuscles) are removed by the membrane filter 55 and pumps (pressures to discharge) the sucked blood, thereby causing the blood to flow down through the path. In FIG. 17, the blood (plasma, blood plasma) S is indicated by a shadow.

Step 3: The blood (plasma, blood plasma) S gradually flows to the air hole 54b side along the flow path 52. The antigen A in the blood (plasma, blood plasma) S binds to the primary antibody $B_1$ that has been immobilized in the first measurement area 58.

Step 4: a solution 63 for labeling is injected from the injection opening 54a. The solution 63 for labeling contains fluorescence labeling substance F modified with the secondary antibody $B_2$.

Step 5: the fluorescence labeling substance F that has been modified with the secondary antibody $B^2$ penetrates into the flow path 52 by a capillary phenomenon. Alternatively, a pump may be connected to the air hole to accelerate reaction, thereby reducing detection time. The pump sucks the blood after blood cells (blood corpuscles) are removed by the membrane filter 55 and pumps (pressures to discharge) the sucked blood, thereby causing the blood to flow down through the path.

Step 6: The fluorescence labeling substance F gradually flows down to the downstream side, and the secondary antibody with which the fluorescence labeling substance F has been modified binds to the antigen A. Consequently, a so-called sandwich in which the antigen A is sandwiched between the primary antibody $B_1$ and the secondary antibody $B_2$ is formed.

As described above, in Steps 1 through 6, the blood is injected from the injection opening and the antigen binds to the primary antibody and the secondary antibody. After Steps 1 through 6, the intensity of fluorescence from the first measurement area 58 is detected, thereby detecting the presence of the antigen and/or the concentration of the antigen. After then, the sample cell 61 is moved in X direction so that the fluorescence signal from the second measurement area 59 can be detected, and the fluorescence signal from the second measurement area 59 is detected. The fluorescence signal from the second measurement area 59 in which the primary antibody $B_0$ that can bind to the secondary antibody $B_2$ is immobilized reflects reaction conditions, such as the amount of the secondary antibody that has flowed down and the activity of the secondary antibody. Therefore, if this signal is used as a reference (reference signal) and the signal from the measurement area is corrected based on the reference, it is possible to obtain a more accurate detection result. Further, a known amount of labeling substance (fluorescence substance and metal particle) may be immobilized in advance in the second measurement area, and the fluorescence signal from the second measurement area 59 may be used as a reference to correct the signal from the first measurement area based on the reference.

An example of a method for modifying the fluorescence labeling substance with the secondary antibody and an example of a method for producing a solution for labeling will be described.

First, a solution containing 50 mM MES buffer and an anti-hCG monoclonal antibody of 5.0 mg/mL (Anti-hCG 5008 SP-5, Medix Biochemica) is added to the fluorescence labeling substance solution (diameter of the fluorescent substance is 500 nm, the excitation wavelength is 502 nm, and the fluorescence wavelength is 510 nm) and stirred. Accordingly, the fluorescence labeling substance is modified with the antibody.

Further, a WSC aqueous solution of 400 mg/mL (No. 02-62-0011, Wako Pure Chemical Industries, Ltd.) is added to the mixture and stirred at a room temperature.

Further, a Glycine aqueous solution of 2 mol/L is added and stirred. Then, particles are caused to precipitate by centrifuge.

Finally, the supernatant is removed, and PBS (pH 7.4) is added. An ultrasonic wash machine is used to cause the fluorescence labeling substance to disperse again. Further, centrifugation is performed, and the supernatant is removed. Then, 500 µL of PBS (pH 7.4) solution of 1% BSA is added, and fluorescence labeling substance is caused to disperse again to obtain a solution for labeling.

<Embodiment 4>

Figure 18:
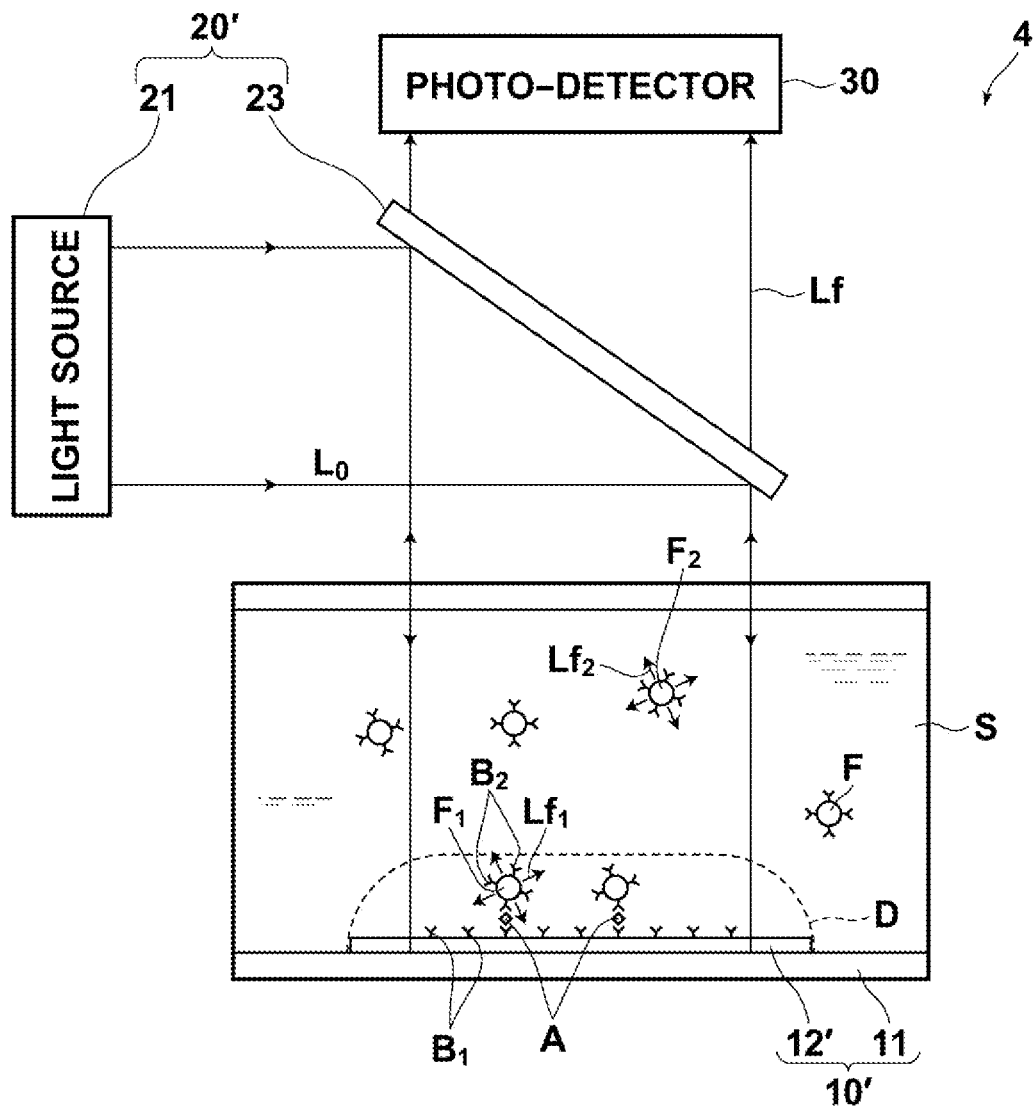
FIG. 18 is a schematic diagram illustrating the structure of an optical signal detection apparatus according to a fourth embodiment of the present invention.

An optical signal detection method according to a fourth embodiment of the present invention and an optical signal detection apparatus used for the method will be described with reference to FIG. 18. FIG. 18 is a diagram illustrating the whole apparatus. FIG. 18 is illustrated in such a manner that the size of each unit or element differs from the actual size thereof for the purpose of explanation. Here, the same reference numerals are assigned to elements that are the same as those of the first embodiment.

In an optical signal detection apparatus 4 illustrated in FIG. 18, a sensor chip 10' and an excitation light irradiation optical system 20' differ from those of the optical signal detection apparatus 1 of the first embodiment.

The sensor chip 10' includes, as a metal layer 12' provided on the dielectric plate 22, a fine metal structure body that generates so-called localized plasmons by irradiation with excitation light $L_0$. The fine metal structure body has an uneven-pattern structure having patterns smaller than the wavelength of the excitation light $L_0$ on the surface thereof. Alternatively, the metal layer 12' may be a plurality of metal nanorods smaller than the wavelength of the excitation light $L_0$. When the sensor chip 10' includes the metal layer 12' that generates localized plasmons as described above, it is not necessary that the excitation light $L_0$ enters the surface between the metal layer 12' and the dielectric plate 11 in such a manner that the excitation light $L_0$ is totally reflected at the interface of the metal layer 12' and the dielectric plate 11. Therefore, here, the excitation light irradiation optical system 20' is structured in such a manner that the excitation light $L_0$ irradiates the dielectric plate 11 from the upper side of the dielectric plate 11.

The excitation light irradiation optical system 20' includes a light source 21 and a half mirror 23. The light source 21 includes a semiconductor laser (LD) or the like that outputs the excitation light $L_0$. The half mirror 23 reflects the excitation light $L_0$ and guides the reflected light to the sensor chip 10'. The half mirror 23, which reflects the excitation light $L_0$, transmits light (fluorescence, scattered light or the like) output or scattered from the photo-reactable labeling substance Lf.

An example of the sensor chip 10' will be described with reference to FIGS. 19A, 19B and 19C.

Figure 19A:
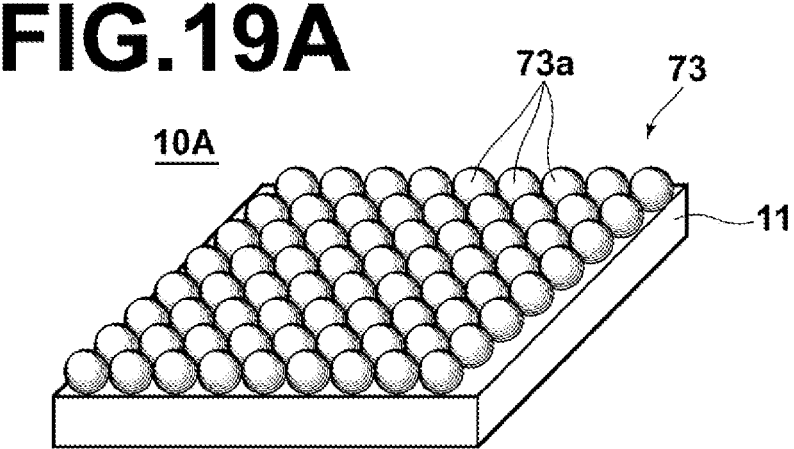
FIG. 19A is a perspective view illustrating a part of a first example of a sensor chip used in the fourth embodiment.

A sensor chip 10A illustrated in FIG. 19A includes the dielectric plate 11 and a fine metal structure body 73. The fine metal structure body 73 is composed of a plurality of metal particles 73a fixed on a predetermined area of the plate 11. The plurality of metal particles 73a are arranged in array form. The arrangement pattern of the metal particles 73a may be appropriately designed. However, it is desirable that the arrangement pattern is substantially regular. This structure is designed in such a manner that an average particle diameter of the metal particles 73a and an average pitch thereof are smaller than the wavelength of the excitation light $L_0$.

Figure 19B:
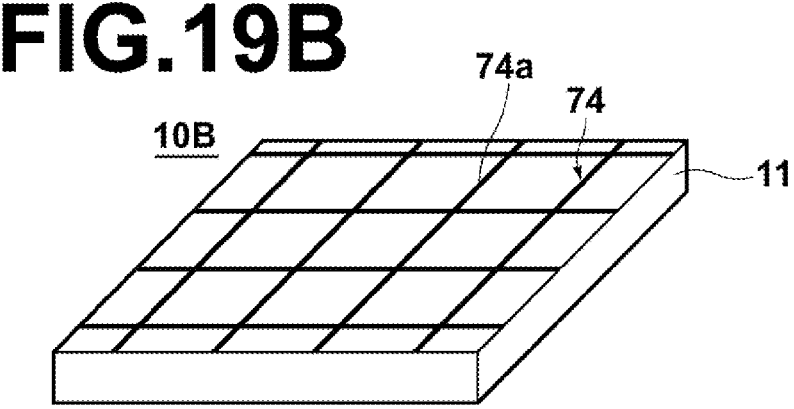
FIG. 19B is a perspective view illustrating a part of a second example of a sensor chip used in the fourth embodiment.

A sensor chip 10B illustrated in FIG. 19B includes the dielectric plate 11 and a fine metal structure body 74. The fine metal structure body 74 is formed by a metal pattern layer. In the metal pattern layer, metal thin wires 74a are arranged in grid form by pattern formation. The arrangement pattern of the metal pattern layer may be appropriately designed. However, it is desirable that the pattern is substantially regular. This structure is designed in such a manner that an average width (line width) of the metal thin wires 74a and an average pitch thereof are smaller than the wavelength of the excitation light $L_0$.

Figure 19C:
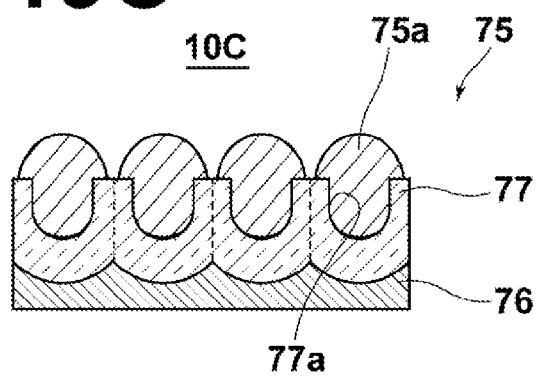
FIG. 19C is a perspective view illustrating a part of a third example of a sensor chip used in the fourth embodiment.

A sensor chip 10C illustrated in FIG. 19C includes a fine metal structure body 75 as disclosed in U.S. Patent Application Publication No. 20070158549. The fine metal structure body 75 is composed of a plurality of mushroom-shape metals 75a that have grown in a plurality of very small holes 77a in a metal oxide object 77. The very small holes 77a are formed in the process of anodic oxidation of a metal 76, such as Al. Here, the metal oxide object 77 corresponds to the dielectric plate 11. The fine metal structure body 75 can be produced by obtaining a metal oxide object ($Al_2O_3$ or the like) by performing anodic oxidation on a part of a metal body (Al or the like) and by causing the metal 75a in each of the plurality of very small holes 77a in the metal oxide object 77 to grow by plating or the like.

In the example illustrated in FIG. 19C, the top portion of the mushroom-shape metal 75a has particle form. Therefore, when the fine metal structure body 75 is observed from the surface of the sample plate, the fine metal structure body 75 is structured in such a manner that metal microparticles are arranged. In this structure, the top portions of the mushroom-shape metals 75a are projections (projections in an uneven pattern). This structure is designed in such a manner that an average diameter of the projections (top portions) and an average pitch thereof are smaller than the wavelength of measurement light L.

Further, as the metal layer 12', which generates localized plasmons by irradiation with excitation light, various kinds of other fine metal structure bodies may be used. The various kinds of fine metal structure bodies utilize fine structures obtained by anodic oxidation on a metal body, and they are disclosed in U.S. Patent Application Publication Nos. 20060234396 and 20060181701, and the like.

Further, the metal layer that generates localized plasmons may be formed by a metal coating the surface of which has been coarsened. As a method for coarsening the surface, there is an electrochemical method utilizing oxidation/reduction or the like. Further, the metal layer may be composed of a plurality of metal nanorods arranged on a sample plate. The metal nanorods have short-axial length of approximately 3 nm to 50 nm and long-axial length of approximately 25 nm to 1000 nm, and the long-axial length should be smaller than the wavelength of the excitation light. The metal nanorods are disclosed, for example, in U.S. Patent Application Publication No. 20070118936, or the like.

Further, it is desirable that the metal fine structure body and the metal nanorods, which are used as the metal layer 12', contains, as a main component, at least one metal selected from the group consisting of Au, Ag, Cu, Al, Pt, Ni and Ti and alloys thereof.

A fluorescence detection method using the optical signal detection apparatus 4, which is structured as described above, will be described.

Excitation light $L_0$ is output from the light source 21 and reflected by a half mirror 23 and enters a sample-contact-surface of the sensor chip 10'. Then, localized plasmons are generated on the surface of the metal layer 12' by irradiation with the excitation light $L_0$. Further, electric field distribution D is generated on the metal layer 12' by the localized plasmons, and an enhanced electric field (region) is formed. Meanwhile, in a region of the sample S, the region being irradiated with the excitation light $L_0$, the fluorescence labeling substance F is exited, and fluorescence is generated. At this time, the intensity of fluorescence $Lf_1$ from fluorescence labeling substance $F_1$ in the enhance electric field is enhanced. However, the intensity of fluorescence $Lf_2$ from fluorescence labeling substance $F_2$ that is not in the enhance electric field is not enhanced. In the photo-detector 30, the fluorescence is condensed by a condensing lens (not illustrated) and detected. At this time, fluorescence from fluorescence labels in a wide region (range) including the enhanced electric field can be condensed. However, for example, if a filter that attenuates fluorescence is provided between the condensing lens and the photo-detector 30, it is possible to detect only fluorescence the intensity of which has been enhanced (increased).

In the fluorescence detection method of this embodiment, sensing is performed by adding fluorescence labeling substance, as fluorescence label F, to substance A to be detected. The fluorescence labeling substance A includes a plurality of fluorescent dye molecules 15 and a light transmissive material 16. The light transmissive material 16 encloses the plurality of fluorescent dye molecules 15 and prevents metal quenching that occurs when the fluorescent dye molecules are close to the metal layer. Since the fluorescent dye molecules 15 are covered by the light transmissive material 16, the fluorescent dye molecules 15 do not directly touch the metal layer. Further, since the plurality of fluorescent dye molecules are enclosed (encapsulated) in the fluorescence labeling substance, it is possible to easily realize a state in which a plurality of fluorescent dye molecules are present in a range within a distance of 10 to 100 nm from the metal layer. Further, complex work or process of providing the SAM coating and the CMD as described above to prevent metal quenching is not necessary. Further, since the fluorescence labeling substance F includes the plurality of fluorescent dye molecules 15, it is possible to greatly increase the fluorescence amount, compared with the conventional method of using the fluorescent dye molecule 15 per se as a label.

<Embodiment 5>

Figure 20:
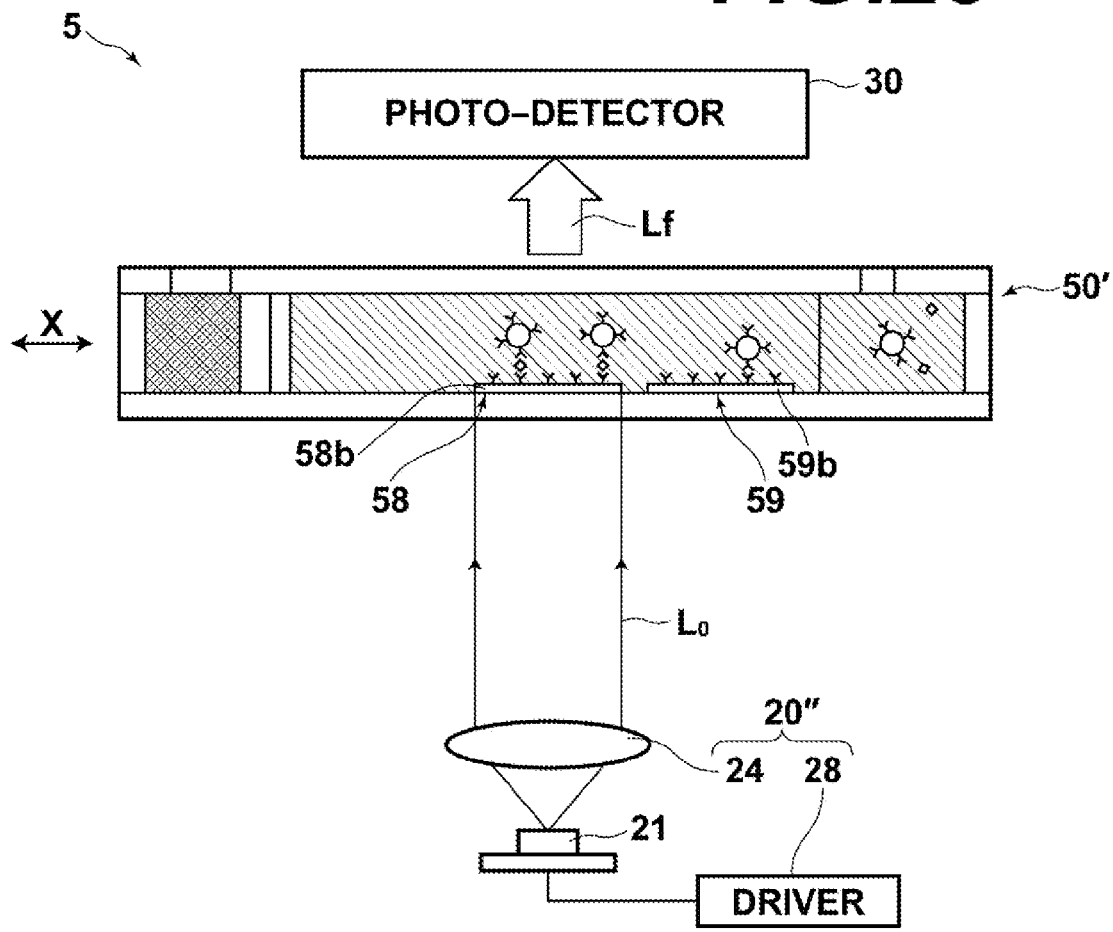
FIG. 20 is a schematic diagram illustrating the structure of an apparatus that is used in an optical signal detection method according to a fifth embodiment of the present invention.

With reference to FIG. 20, an optical signal detection method and apparatus 5 according to a fifth embodiment of the present invention will be described. In the fifth embodiment, the same reference numerals are assigned to elements that are the same as those of the second embodiment.

The optical signal detection apparatus 5 illustrated in FIG. 20 includes a sample cell 50' and an excitation light irradiation optical system 20". In the sample cell 50', fine metal structure bodies 58b and 59b, as metal layers, are provided at predetermined regions (measurement areas 58 and 59) on the base, which is formed by a dielectric plate. The excitation light irradiation optical system 20" irradiates the measurement areas 58 and 59 with excitation light $L_0$ from the lower sides of the measurement areas 58 and 59. The excitation light is transmitted through the base. In the optical signal detection apparatus (fluorescence detection apparatus) 5, an enhanced electric field is generated by localized plasmons that have been generated by irradiation of the fine metal structure 58b with the excitation light. In the fluorescence detection apparatus 5, fluoresce enhanced in the enhanced electric field is measured.

The optical signal detection method (fluorescence detection method) and an assay method are similar to those of the second embodiment. In the present embodiment, sensing is performed by adding fluorescence labeling substance F to substance A to be detected. The fluorescence labeling substance A includes a plurality of fluorescent dye molecules 15 and a light transmissive material 16. The light transmissive material 16 encloses the plurality of fluorescent dye molecules 15 and prevents metal quenching that occurs when the fluorescent dye molecules are close to the metal layer. Since the fluorescent dye molecules 15 are covered by the light transmissive material 16, the fluorescent dye molecules 15 do not directly touch the metal layer. Further, since the plurality of fluorescent dye molecules are enclosed (encapsulated) in the fluorescence labeling substance, it is possible to easily realize a state in which a plurality of fluorescent dye molecules are present in a range within a distance of 10 to 100 nm from the metal layer. Further, complex work or process of providing the SAM coating and the CMD as described above to prevent metal quenching is not necessary. Further, since the fluorescence labeling substance F includes the plurality of fluorescent dye molecules 15, it is possible to greatly increase the fluorescence amount, compared with the conventional method of using the fluorescent dye molecule 15 per se as a label.

Figure 21:
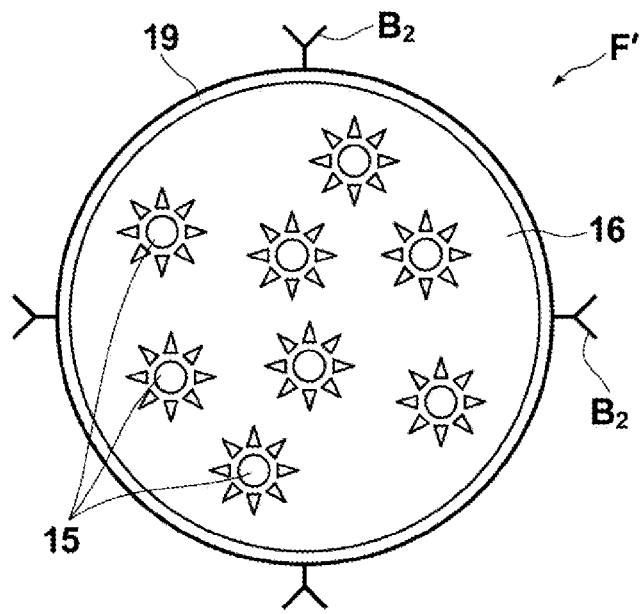
FIG. 21 is a schematic diagram illustrating fluorescence labeling-substances having a metal coating (photo-reactable labeling-substance)

In each of the aforementioned embodiments, the fluorescence labeling substance F includes a multiplicity of fluorescent dye molecules 15 and the light transmissive material 16 that encloses the multiplicity of fluorescent dye molecules 15 to prevent metal quenching. Further, as illustrated in FIG. 21, a metal coating 19 that is sufficiently thin to transmit fluorescence may be provided on the surface of the fluorescence labeling substance F. The metal coating 19 may cover the entire surface of the light transmissive material 16. Alternatively, the metal coating 19 may cover the light transmissive material 16 in such a manner that a part of the light transmissive material 16 is exposed. As the material for the metal coating 19, a metal material similar to the material of the aforementioned metal layer may be used.

When the metal coating 19 is provided on the surface of the fluorescence labeling substance (photo-reactable labeling substance) F, surface plasmons or localized plasmons that have generated in the metal layers 12 and 12' of the sensor chips 10 and 10' are coupled with a whispering gallery mode of the metal coating 19 of the fluorescence labeling substance F. Therefore, it is possible to more efficiently excite the fluorescent dye molecules 15 in the fluorescence labeling substance F. The whispering gallery mode is an electromagnetic-wave mode that is localized on the surface of a very small ball (sphere), such as the fluorescence labeling substance having less than or equal to approximately (φ5300 nm, which is used in this embodiment, and goes around the surface.

The fluorescence labeling substance (photo-reactable labeling substance) F' coated with the metal may be used in a manner similar to the fluorescence labeling substance F in the first through fifth embodiments, for example, by modifying the surface of the metal coating 19 with second bonding substance (secondary antibody) $B_2$ that specifically binds to detection target substance (antigen) A to be detected.

An example of a method for applying metal coating to the fluorescence labeling substance will be described.

First, fluorescence labeling substance is produced through the aforementioned procedures. The surface of the fluorescence labeling substance is modified with polyethyleneimine (PEI) (EPOMIN, Nippon Shokubai Co., Ltd.).

Next, PEI on the surface of the particle is caused to adsorb Pd nanoparticle having the particle diameter of 15 nm (average particle diameter of 19 nm, Tokuriki-Honten).

The polystyrene particles that have adsorbed the Pd nanoparticles are soaked in non-electrolyzed plating solution (HAuCl$_4$, Kojima Chemicals Co., Ltd.). Non-electrolysis using the Pd nanoparticles as a catalyst is utilized, and metal coating is formed on the surface of the polystyrene particles.

Figure 22:
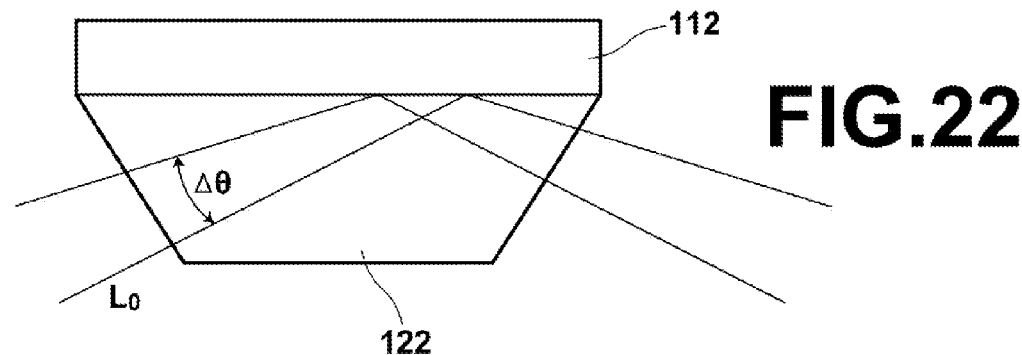
FIG. 22 is a diagram illustrating another embodiment of an excitation light irradiation optical system.

In each of the aforementioned embodiments, the excitation light L$_0$ enters the interface at predetermined angle θ as parallel light. The excitation light L$_0$ may be a fan beam (focused light) that has angle width Δθ with respect to angle θ, as schematically illustrated in FIG. 22. When the excitation light L$_0$ is the fan beam, the excitation light L$_0$ enters the interface between a prism 122 and a metal layer (coating) 112 on the prism at an incidence angle in the range of (angle θ−Δθ/2) to (angle θ+Δθ/2). If a resonance angle is present in this range of angles, surface plasmons can be excited in the metal layer 112. The refractive index of the medium on the metal layer before the sample is supplied to the surface of the metal layer and the refractive index after the sample is supplied differ from each other. Therefore, the resonance angle at which the surface plasmons are generated changes. When the parallel light is used as the excitation light as in the aforementioned embodiments, it is necessary to adjust the incidence angle of the parallel light each time when the resonance angle changes. However, when the fan beam as illustrated in FIG. 22, which enters the interface at incidence angles that have a certain width, is used, it is not necessary to adjust the incidence angle every time when the resonance angle changes. Further, it is desirable that the fan beam has intensity of flat distribution so that the intensity does not fluctuate according to the incidence angles.

Further, in each of the aforementioned embodiments, a case of performing an assay using a sandwich method, which is a non-competition method, has been described. Further, the optical signal detection method and apparatus, sample cell and measurement kit of the present invention may be applied to an assay using a competition method instead of the sandwich method.

Figure 23:
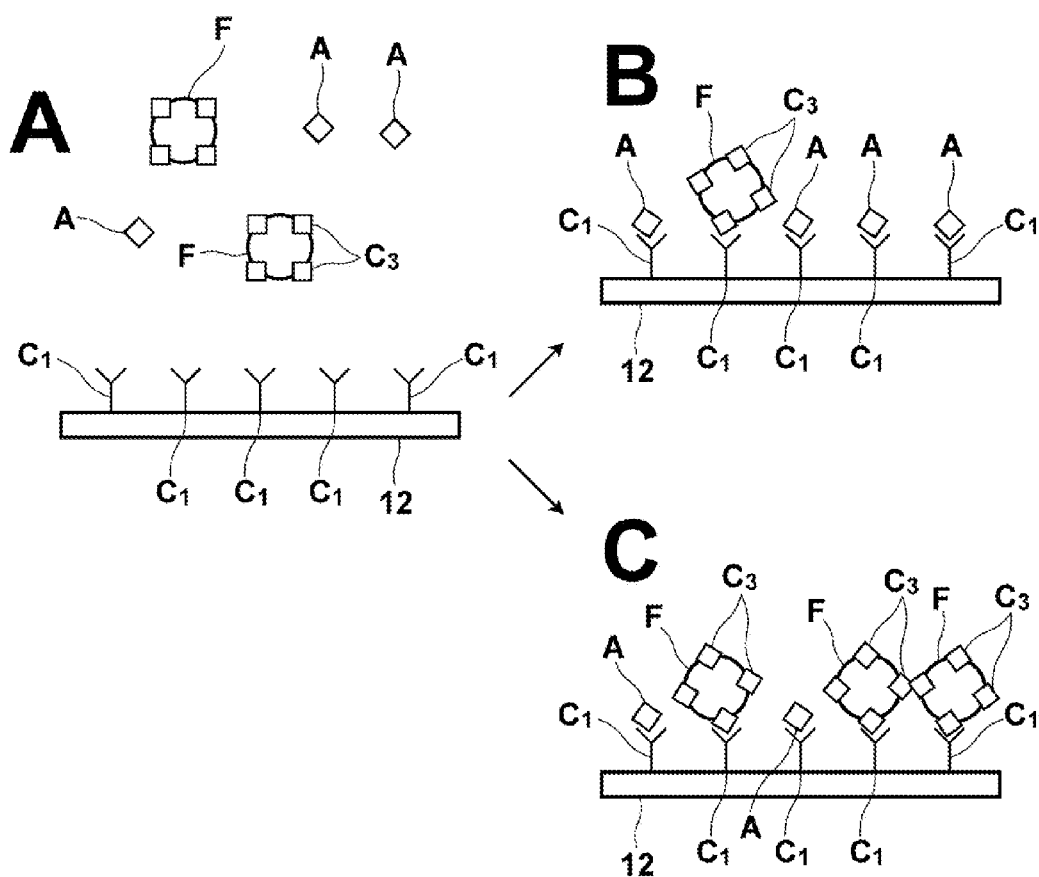
FIG. 23 is a schematic diagram for explaining the principle of a competition method.

With reference to FIG. 23, the competition method will be described.

As A in FIG. 23 illustrates, the fluorescence labeling substance F is modified with third bonding substance C$_3$ that exhibits the same immune reaction as that of the substance to be detected (for example, antigen). Further, first binding substance C$_1$ (for example, primary antibody) that specifically binds to each of the substance A to be detected and the third bonding substance C$_3$ is immobilized on the metal layer 12. The fluorescence labeling substance F modified with the third bonding substance C$_3$ (for example, competitive antigen) of a predetermined concentration is mixed with the substance A to be detected. The mixture is caused to competitively react with the first binding substance C$_1$ that has been immobilized on the metal layer 12 (antigen-antibody reaction). The concentration of the fluorescence labeling substance at the time of mixing the antigen and the fluorescence labeling substance is a known value.

As B in FIG. 23 shows, in the competition method, when the concentration of the substance A to be detected is higher, the amount of the third bonding substance C$_3$ that binds to the first binding substance C$_1$ is lower. In other words, as the number of particles of the fluorescence labeling substance F on the metal layer 12 becomes smaller, the intensity of fluorescence becomes lower. In contrast, as C in FIG. 23 shows, when the concentration of the substance A to be detected is lower, the amount of the third bonding substance C$_3$ that binds to the first binding substance C$_1$ is higher. In other words, as the number of particles of the fluorescence labeling substance F on the metal layer 12 becomes larger, the intensity of fluorescence becomes higher. In the competition method, measurement is possible if one epitope is present in the substance to be detected. Therefore, the competition method is suitable to detect a substance that has low molecular weight.

Figure 24:
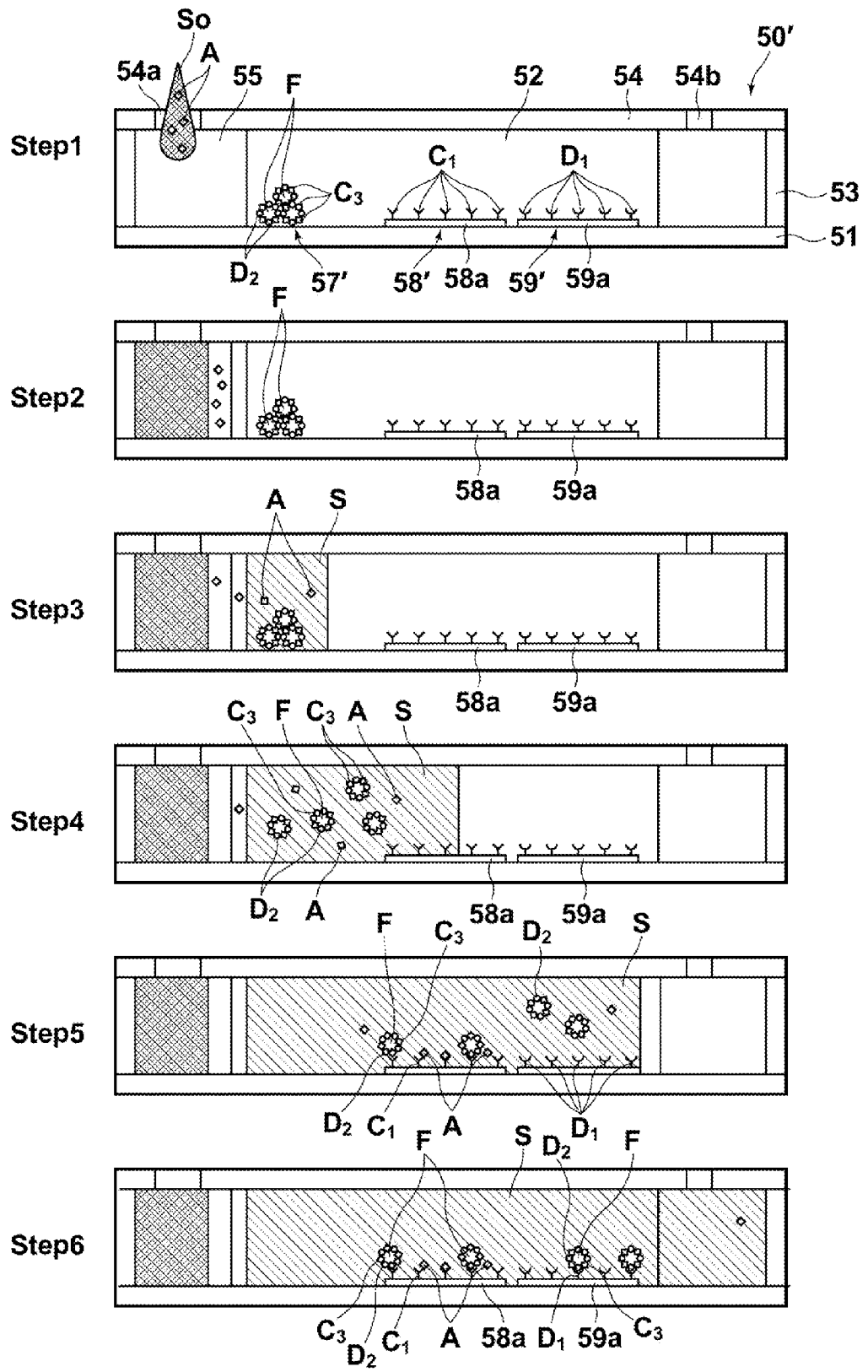
FIG. 24 is a diagram illustrating an assay (competition method) using a sample cell in another embodiment of the present invention.

FIG. 24 is a diagram illustrating assay procedures using a competition method. In the assay procedures, the sample cell 50' according to another embodiment of the present invention is used. In the fluorescence detection apparatus 2 in the second embodiment, the sample cell 50' may be used instead of the sample cell 50. In the sample cell 50', an antibody provided in the flow path differs from the antibody provided in the flow path of the sample cell 50. The sample cell 50' of the present embodiment is adopted in an assay using the competition method.

In the sample cell 50', a labeling secondary antibody adsorption area 57', a first measurement area (sensor portion) 58', and a second measurement area (reference portion) 59' are sequentially formed on the base 51 of the sample cell 50' from the upstream side of the flow path 52. In the labeling secondary antibody adsorption area 57', fluorescence labeling substance F the surface of which is modified with the competitive antigen C$_3$ (third binding substance) that competes with the antigen A, which is the substance to be detected, and specifically binds to a primary antibody that will be described later has been physically adsorbed. In the first measurement area 58', a primary antibody (first binding substance) C$_1$ is immobilized. The primary antibody C$_1$ specifically binds to the antigen A, which is the substance to be detected, and the competitive antigen C$_3$. In the second measurement area 59', a substance D$_1$ is immobilized. The substance D$_1$ specifically binds neither to the antigen A, which is the substance to be detected, nor to the competitive antigen C$_3$. The substance D$_1$ constitutes one of a pair of different immune reaction substances.

In the competition method, it is necessary to immobilize the substance D$_1$ that constitutes one of a pair of different immune reaction substances and that specifically binds neither to the antigen C$_3$ nor the primary antibody C$_1$ in the second measurement area 59' that is used for signal calibration. Further, the surface of the fluorescence labeling substance F is modified with substance D$_2$ that constitutes the other one of the pair of different immune reaction substance and the competitive antigen C$_3$. As the combination of the substances D$_1$ and D$_2$, for example, avidin—biotin may be used.

In the sample cell 50', the structure of the first measurement area 58' and the structure of the second measurement area 59' are the same except that different substances are immobilized on the Au coating 58a and the Au coating 59a, respectively. Specifically, in the first measurement area 58', the primary antibody C$_1$ is immobilized on the Au coating 58a in the first measurement area 58', and the substance D$_1$ is immobilized on the Au coating 59a in the second measurement area 59'. The antigen A and the competitive antigen C$_3$ competitively bind to the primary antibody C$_1$ immobilized in the first measurement area 58'. The object immobilized in the second measurement area 59' binds neither to the antigen A nor the competitive antigen C$_3$, but specifically binds to the substance D$_2$ with which the surface of the fluorescence labeling substance F is modified together with the competitive antigen C$_3$. Accordingly, it is possible to detect fluctuation factors related to reaction, such as the amount and activity of the competitive antigen that has flowed through the flow path, and fluctuation factors related to the degree of enhancement of the surface plasmons, such as the excitation light irradiation optical system 20, the gold (Au) layer 58a, the gold (Au) layer 59a, and the liquid sample S, to use the detected fluctuation factors for calibration. Further, a known amount of labeling substance other than the substance D$_1$ may be immobilized in advance in the second measurement area. The labeling substance may the same kind of substance as the fluorescence labeling substance the surface of which has been modified with the secondary antibody. Alternatively, the labeling substance may be a substance having wavelength and size that are different from those of the fluorescence labeling substance the surface of which has been modified with the secondary antibody. In this case, only the fluctuation factors related to the degree of enhancement of the surface plasmons, such as the excitation light irradiation optical system 20, the gold (Au) layers 58$a$ and 59$a$ and the liquid sample S to use the detected fluctuation factors for calibration. Further, whether the substance D1 or the known amount of the labeling substance is immobilized in the second measurement area 59' may be appropriately selected based on the purpose and method for calibration.

Next, assay procedures will be described. In the assay procedures, blood (whole blood) is injected to the sample cell 50' from the injection opening, and an assay is performed. The blood is the assay target (examination target) as to whether an antigen, which is a substance to be detected, is included.

Step 1: Blood (whole blood) $S_0$, which is the assay target, is injected from an injection opening 54$a$. Here, a case in which the antigen that is the substance to be detected is included in the blood $S_0$ will be described. In FIG. 24, the blood (whole blood) $S_0$ is indicated by a mesh.

Step 2: The blood (whole blood) $S_0$ is filtered by a membrane filter 55, and large molecules, such as erythrocyte (red blood cells) and leukocyte (white blood cells) remain as the residue.

Step 3: The blood (plasma, blood plasma) S after blood cells (blood corpuscles) are removed by the membrane filter 55 penetrates into the flow path 52 by a capillary phenomenon. Alternatively, a pump may be connected to the air hole 54$b$ to accelerate reaction, thereby reducing detection time. The pump sucks the blood after blood cells (blood corpuscles) are removed by the membrane filter 55 and pumps (pressures to discharge) the sucked blood, thereby causing the blood to flow down through the path. In FIG. 24, the blood (plasma, blood plasma) S is indicated by a shadow.

Step 4: The blood (plasma, blood plasma) S that has penetrated into the flow path 52 and the fluorescence labeling substance F to which the competitive antigen $C_3$ has been added are mixed together.

Step 5: The blood (plasma, blood plasma) S gradually flows to the air hole 54$b$ side along the flow path 52. The antigen A and the competitive antigen $C_3$ competitively bind to the primary antibody $C_1$ that has been immobilized in the first measurement area 58'.

Step 6: A part of the fluorescence labeling substance F that is modified with the competitive antigen $C_3$ that has not bound to the primary antibody $C_1$ on the first measurement area 58' binds to the substance $D_1$ immobilized on the second measurement area 59' and immobilized in the measurement area 59'. Further, even if the fluorescence labeling substance that has bound neither to the primary antibody $C_1$ nor to the substance $D_1$ through the competitive antigen $C_3$ or the substance $D_2$, respectively, remains in the measurement area, the blood (plasma, blood plasma) S flowing so as to follow functions as washing liquid, and washes away a floated substance and a non-specifically-adsorbed substance.

As described above, in Steps 1 through 6, the blood is injected from the injection opening and the antigen A and the competitive antigen $C_3$ competitively bind to the primary antibody $C_1$ on the first measurement area 58'. After Steps 1 through 6, the intensity of fluorescence from the first measurement area 58' and the second measurement area 59' are detected, thereby obtaining the presence of the antigen and/or the concentration of the antigen.

In the fluorescence detection method using the sample cell of the present embodiment, the fluorescence labeling substance F is used. Therefore, an advantageous effect similar to each of the aforementioned embodiment can be achieved. It is possible to perform accurate measurement by using a simple method.

In each of the embodiments, the concentration may be obtained based on detected signals. Specifically, when a predetermined time period has passed after the start of binding of the binding substance, to which the photo-reactable labeling-substance was attached, to the sensor portion, an optical signal (fluorescence in the aforementioned case) is detected. It is possible to obtain the concentration of the substance to be detected (the amount of the substance to be detected) based on the value of the detected optical signal (the intensity of the optical signal). The concentration of the substance to be detected is obtained from a calibration curve showing the relation between the intensity of the optical signal and the concentration, and the calibration curve is obtained in advance. Further, a point in time when binding of the binding substance to the sensor portion is started (a point in time when binding starts, or the start of binding) may be a point in time when a reaction liquid containing the photo-reactable labeling-substance and a sample liquid that are mixed together is started to be poured onto the sensor chip. Alternatively, when after the sample liquid is poured onto the sensor chip, a solution containing the photo-reactable labeling-substance is poured, the point in time when binding of the binding substance to the sensor portion is started may be a point in time when a solution containing the photo-reactable labeling-substance is started to be poured, or the like.

Further, for the purpose of assaying the amount of the substance to be detected at a higher S/N ratio, it is desirable to detect optical signals at a plurality of different points in time after the start of binding of the binding substance, to which the photo-reactable labeling-substance has been attached, to the sensor portion. It is desirable that the concentration is obtained based on a temporal change in the value of the optical signals, and the concentration of the substance to be detected is obtained from a calibration curve showing the relation between the temporal change in the optical signals and the concentration. The calibration curve is obtained in advance. Further, the detected optical signals include a noise component, such as an apparatus noise (a noise caused by the apparatus), which does not change temporally. However, the temporal change (gradient) in the optical signals does not contain such a noise component. Further, since the signals are obtained at a plurality of points in time, it is possible to reduce the influence of the dispersion of measurement values. Hence, it is possible to improve the accuracy of assay compared with the method of detecting the optical signal only once after a predetermined time period has passed.

Next, an example of measurement to obtain a calibration curve showing the relation between the temporal change in the intensity of the optical signal and the concentration will be described. The calibration curve is used in a method for obtaining the amount (concentration) of the substance to be detected by detecting optical signals at a plurality of different points in time. In the method, the amount of the substance to be detected is obtained based on a temporal change in the intensity of the light.

"Preparation of Solution Containing Anti-hCG-Antibody-Bound Photo-Reactable Labeling-Substance"

First, a 250 μL of solution containing anti-hCG monoclonal antibodies of 2 mg/mL (#100006, manufactured by Medix Co.) and an MES buffer of 50 mM (pH 6.0) was added to a 250 μL of solution containing fluorescent labeling substance of 2%, and stirred at room temperature for 15 minutes. Further, a 5 μL of aqueous solution of WSC (No. 01-62-0011, manufactured by Wako Pure Chemical Industries, Ltd.) of 10 mg/mL was added, and stirred at room temperature for two hours. Further, a 25 μL of aqueous solution of Glycine of 2 mol/L was added, and stirred for 30 minutes and centrifuged (15,000 rpm, 4° C., 15 minutes) to precipitate the fluorescent labeling substance. Further, the supernatant was removed, and a 500 μL of PBS solution (pH 7.4) was added. The fluorescent labeling substance was dispersed again by using an ultrasonic wash machine, and centrifuged (15,000 rpm, 4° C., 15 minutes). Further, the supernatant was removed, and a 500 μL of PBS (pH 7.4) solution containing BSA of 1% was added, and the fluorescent labeling substance was dispersed again. Accordingly, a solution containing anti-hCG-antibody-bound fluorescent substance of 1% (w/v) was obtained.

"Preparation of Anti-hCG-Antibody-Bound Measurement Area"

Before an upper plate is attached to the flow path of the sensor chip, 100 μL of 150 mM sodium chloride solution containing anti-hCG monoclonal antibodies (#100066, manufactured by Medix Co.) that had been prepared at 10 μg/mL was added, and kept static at room temperature for one hour. Further, the solution containing the antibodies was removed from the measurement area, and the measurement area was washed (300 μL/time, three times) by using a buffer for washing (PBS (pH 7.4) containing 0.05% (w/v) Tween-20) that had been prepared in advance. After the measurement area was washed, 300 μL of PBS (pH 7.4) containing casein of 1% was added to block a portion that had not adsorbed antibodies, and kept static at room temperature for one hour. The measurement area was washed by using the aforementioned buffer for washing, and 300 μL of Immunoassay Stabilizer (manufactured by ABI, Co.), as a stabilizer, was added to each well, and left at room temperature for 30 minutes. Further, the solution was removed, and the moisture was completely removed in a dryer. Further, after anti-hCG-antibody binding processing;, a lid member was used to seal the flow path of the sensor chip, and a flow-path-type sensor chip was produced. An ultrasonic welding method or the like may be used to seal the flow path.

"Measurement of hCG-Antigen Using Anti-hCG-Antibody-Bound Fluorescent Labeling Substance"

PBS solutions (phosphoric acid buffer) containing BSA of 1%, as sample solutions, were prepared by adding purified hCG antigens of 0 p, 0.9 pM, 9 pM and 90 pM, respectively. When the concentration of the purified hCG antigens is 0 p, the prepared PBS solution is exactly the PBS solution containing BSA of 1%.

Further, 5 pL of solution containing anti-hCG-antibody-bound photo-reactable labeling-substance of 1% that had been prepared as described above was added to each of 500 μL of sample solutions, and mixed to obtain reaction liquids. A sample cell similar to the sample cells illustrated in FIGS. 3A and 3B was used, and fluorescent signals from the measurement area was measured at a plurality of different points in time while the reaction liquid was caused to flow down on the measurement area. At this time, a pump was connected to an air hole of the sample cell, and suction was performed by the pump so that the flow speed becomes constant (linear velocity of 1.4 mm/s). Measurement was performed while a 300 μL of reaction liquid was sent to the measurement area.

Figure 25:
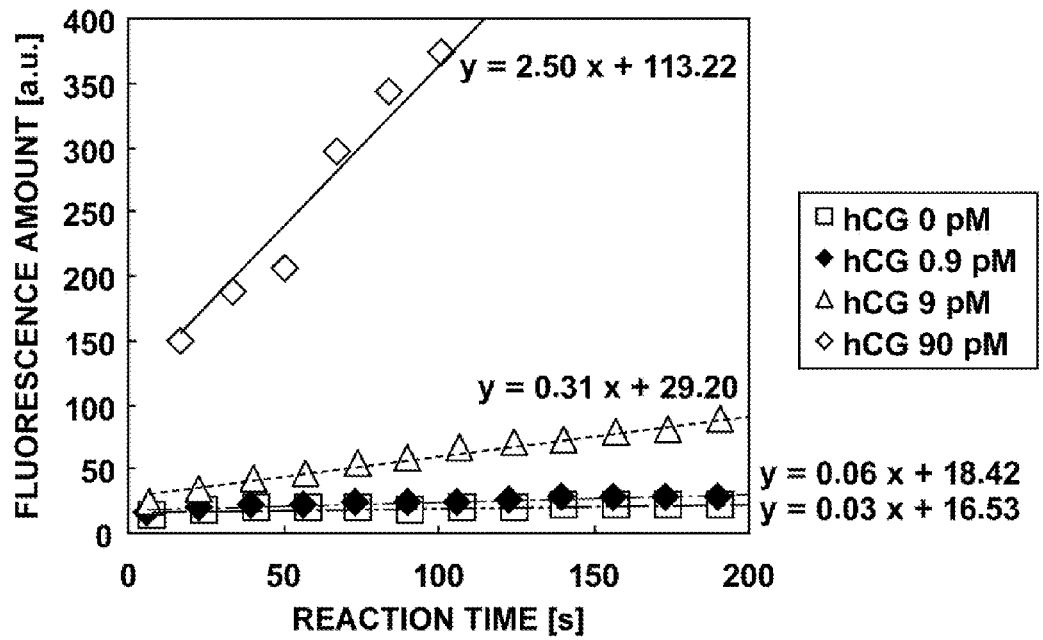
FIG. 25 is a diagram illustrating temporal changes in signals measured in an optical signal detection method according to a sixth embodiment of the present invention.

FIG. 25 illustrates the result of measurement of a temporal change in the intensity of a fluorescent signal for each of reaction liquids that have respective concentrations, as described above. It is possible to obtain, based on the measurement result illustrated in FIG. 25, a temporary change (gradient a) in a fluorescence amount for each hCG concentration. Specifically, as illustrated in FIG. 25, straight line fitting was performed for each concentration, and the following formula was obtained: y=ax+b.

Figure 26:
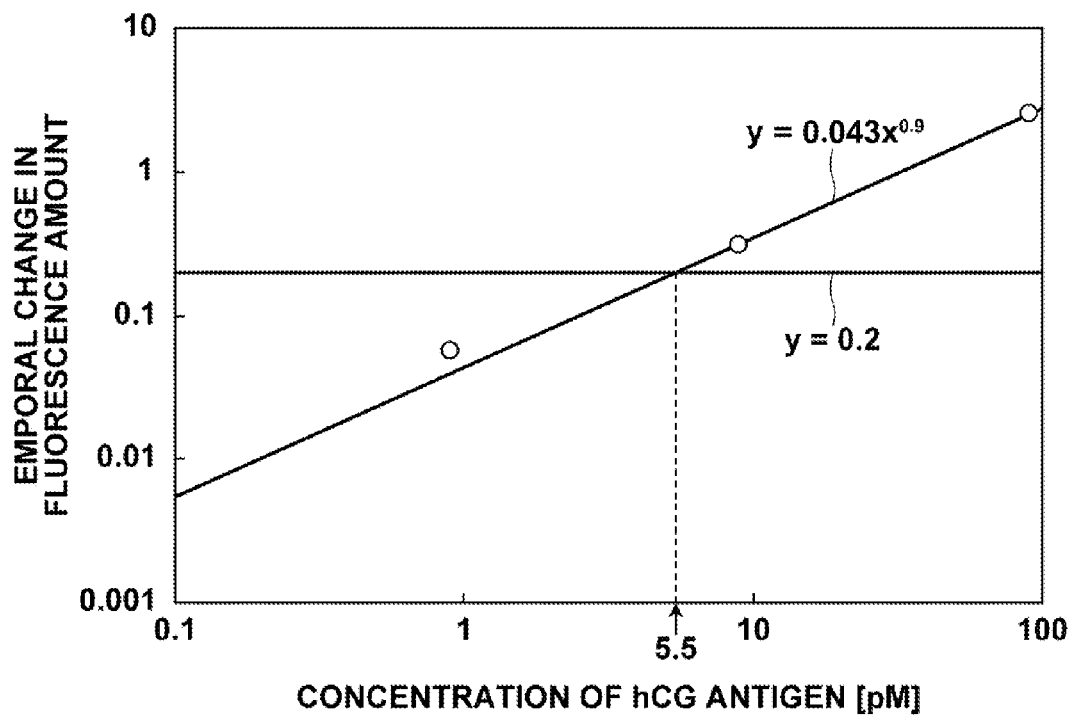
FIG. 26 is a diagram illustrating relation between temporal changes in optical signals and concentration (calibration curve)

Further, the temporal change (gradient a) in the fluorescence amount obtained in FIG. 25 was plotted on y-axis, and the concentration was plotted on x-axis. Accordingly, the calibration curve of the relation between the temporal change in the fluorescence amount and the concentration, as illustrated in FIG. 26, was obtained. Here, it was possible to represent the relation between the hCG antigen concentration (x) and the temporal change (y) in the fluorescence amount as follows: $y=0.043x^{0.9}$. For example, with respect to a sample containing hCG antigens of an unknown concentration, when the temporal change in the fluorescence amount is measured, if the temporal change (gradient) is 0.2, the concentration (5.5 pM) at the intersection of $y=0.043x^{0.9}$ and $y=0.2$ in FIG. 26 can be identified as the concentration.

Further, as an optical signal detection system, it is desirable that the obtained calibration curve about the temporal change in the optical signal and the concentration of the substance to be detected (hCG antigen in the above example) is obtained for each substance to be detected, and stored in a predetermined storage unit. Accordingly, it becomes possible to identify, based on the calibration curve corresponding to each substance to be detected, the amount (concentration) of the substance to be detected in the sample solution. Specifically, when the amount (concentration) of the substance to be detected in the sample liquid needs to be identified, the sensing method that has been described in each of the aforementioned embodiments may be used. Further, optical signals may be detected at a plurality of different points in time from a point in time when the binding substance is started to bind to the sensor portion (measurement area), and a temporal change in the intensity of the optical signals may be obtained. Further, with respect to the obtained temporal change in the intensity of the optical signal, a calibration curve corresponding to the substance to be detected should be referred to, and a concentration that corresponds to the temporal change in the intensity of the optical signal should be identified.

In the example of measuring the calibration curve, straight line fitting using a linear function was performed to obtain the temporal change (gradient) in the fluorescence amount. Alternatively, fitting may be performed by using a different function, such as an exponential function. Note that when the concentration of a substance to be detected, the concentration being unknown, needs to be identified, the same function as the function that was used to obtain the calibration curve which is referred to should be used.

Further, in the surface-plasmon-enhanced fluorescence detection apparatus, there has been a problem that fluorescent molecules cause metal quenching on the surface of the metal, as described in the section of "Description of the Related Art". Therefore, it has not been easy to produce the surface-plasmon-enhanced fluorescence detection apparatus to be sold as a product. However, the problem of the metal quenching can be solved by producing a fluorescence labeling substance to which metal-quenching prevention structure has been added and by using the fluorescence labeling substance as a label. Further, the fluorescent dye molecules are enclosed by the light transmissive material to prevent metal quenching. Therefore, it is possible to isolate the fluorescent dye from ozone in air, which accelerates discoloration of the fluorescent dye, and a quencher in a solvent, which has a quenching effect. Accordingly, an unexpected advantageous effect that the stability of the dye increases has been obtained. These various advantageous effects have made it possible to overcome an obstacle to commercialization of the surface-plasmon-enhanced fluorescence detection apparatus, thereby realizing the commercialization.

What is claimed is:

1. An optical signal detection method comprising the steps of:
   preparing a sensor chip including a dielectric plate and a sensor portion having a metal layer deposited on a predetermined area of a surface of the dielectric plate;
   binding a binding substance of an amount corresponding to the amount of a substance to be detected that is included in a sample to the sensor portion by contacting the sample with the sensor portion of the sensor chip, the binding substance having a photo-reactable labeling-substance attached to the binding substance; and
   obtaining the amount of the substance to be detected by irradiating the predetermined area with excitation light and by detecting light output from the photo-reactable labeling-substance in an enhanced electric field that has been generated on the metal layer by irradiation with the excitation light, wherein the photo-reactable labeling-substance includes a plurality of molecules of a photo-reactable substance enveloped by a light transmissive material that transmits light output from the plurality of molecules of the photo-reactable substance to prevent metal quenching that occurs when the photo-reactable substance is located close to the metal layer, and said photo-reactable labeling substance is used as a label, and said plurality of molecules enveloped within the light transmissive material are disposed within a sample solution including said sample.

2. An optical signal detection method, as defined in claim 1, wherein the light output from the photo-reactable labeling-substance is detected at a plurality of different points in time, and wherein the amount of the substance to be detected is obtained based on a temporal change in the intensity of the light.

3. An optical signal detection method, as defined in claim 1, wherein the particle diameter of the photo-reactable labeling-substance is less than or equal to 5300 nm.

4. An optical signal detection method, as defined in claim 1, wherein the particle diameter of the photo-reactable labeling-substance is in the range of 70 nm to 900 nm.

5. An optical signal detection method, as defined in claim 1, wherein the photo-reactable substance produces fluorescence by irradiation with the excitation light, and wherein the particle diameter of the photo-reactable labeling-substance is in the range of 90 nm to 700 nm.

6. An optical signal detection method, as defined in claim 1, wherein the photo-reactable substance produces fluorescence by irradiation with the excitation light, and wherein the particle diameter of the photo-reactable labeling-substance is in the range of 130 nm to 500 nm.

7. An optical signal detection method, as defined in claim 1, wherein the photo-reactable substance produces fluorescence by irradiation with the excitation light, and wherein a metal coating is provided on the surface of the photo-reactable labeling-substance in such a manner that the thickness of the metal coating is sufficiently thin to transmit the fluorescence.

8. An optical signal detection apparatus comprising:
   a sensor chip including a dielectric plate and a sensor portion having a metal layer deposited on a predetermined area of a surface of the dielectric plate;
   an excitation-light irradiation optical system that irradiates the predetermined area with excitation light;
   a light detection means, wherein when a sample is contacted with the sensor portion, if a binding substance of an amount corresponding to the amount of a substance to be detected that is included in the sample binds to the sensor portion, the binding substance having a photo-reactable labeling-substance attached to the binding substance, the light detection means detects light output from the photo-reactable labeling-substance in an enhanced electric field that has been generated on the metal layer by irradiating the sensor chip with the excitation light, and wherein the photo-reactable labeling-substance includes a plurality of molecules of a photo-reactable substance enclosed by a light transmissive material that transmits light output from the plurality of molecules of the photo-reactable substance to prevent metal quenching that occurs when the photo-reactable substance is located close to the metal layer.

9. A sample cell for detecting an optical signal, wherein the sample cell is used in an optical signal detection method for detecting light output from a photo-reactable labeling-substance, the sample cell comprising:
   a base having a flow path through which a liquid sample flows down;
   an injection opening for injecting the liquid sample into the flow path, the injection opening being provided on the upstream side of the flow path;
   an air hole for causing the liquid sample injected from the injection opening to flow toward the downstream side of the flow path, the air hole being provided on the downstream side of the flow path;
   a sensor chip portion provided in the flow path between the injection opening and the air hole, the sensor chip portion including a dielectric plate that is provided on at least a part of the inner wall of the flow path and a metal layer that is provided in a predetermined area on a sample-contact-side surface of the dielectric plate;
   a first binding substance immobilized on the metal layer, the first binding substance specifically binding to a substance to be detected; and
   a photo-reactable labeling-substance immobilized at a position in the flow path, the position being on the upstream side of the sensor chip portion, and wherein the photo-reactable labeling-substance is modified with a second binding substance that specifically binds to the substance to be detected or by a third binding substance that specifically binds to the first binding substance and that competes with the substance to be detected, wherein
   the photo reactable labeling-substance includes a plurality of molecules of photo reactable substance enclosed by a light transmissive material that transmits light output from the plurality of molecules of the photo reactable substance to prevent metal quenching that occurs when the photo reactable substance is located close to the metal layer.

10. A sample cell for detecting an optical signal, as defined in claim 9, wherein the particle diameter of the photo-reactable labeling-substance is less than or equal to 5300 nm.

11. A sample cell for detecting an optical signal, as defined in claim 9, wherein the particle diameter of the photo-reactable labeling-substance is in the range of 70 nm to 900 nm.

12. A sample cell for detecting an optical signal, as defined in claim 9, wherein the photo-reactable substance produces fluorescence by irradiation with the excitation light, and wherein the particle diameter of the photo-reactable labeling-substance is in the range of 90 nm to 700 nm.

13. A sample cell for detecting an optical signal, as defined in claim 9, wherein the photo-reactable substance produces fluorescence by irradiation with the excitation light, and wherein the particle diameter of the photo-reactable labeling-substance is in the range of 130 nm to 500 nm.

14. A sample cell for detecting an optical signal, as defined in claim 9, wherein the photo-reactable substance produces fluorescence by irradiation with the excitation light, and wherein a metal coating is provided on the surface of the photo-reactable labeling-substance in such a manner that the thickness of the metal coating is sufficiently thin to transmit the fluorescence.

15. A kit for detecting an optical signal, wherein the kit is used in an optical signal detection method for detecting light output from a photo-reactable labeling- substance, the kit comprising:
 a sample cell; and
 a solution for labeling,
 and wherein the sample cell includes:
 a base having a flow path through which a liquid sample flows down;
 an injection opening for injecting the liquid sample into the flow path, the injection opening being provided on the upstream side of the flow path;
 an air hole for causing the liquid sample injected from the injection opening to flow toward the downstream side of the flow path, the air hole being provided on the downstream side of the flow path;
 a sensor chip portion provided in the flow path between the injection opening and the air hole, the sensor chip portion including a dielectric plate that is provided on at least a part of the inner wall of the flow path and a metal layer that is provided in a predetermined area on a sample-contact-side surface of the dielectric plate; and
 a first binding substance immobilized on the metal layer, the first binding substance specifically binding to a substance to be detected,
 and wherein when optical signal detection is performed, the solution for labeling is caused to flow down through the flow path together with the liquid sample or after the liquid sample flows down through the flow path, and wherein the solution for labeling contains a photo-reactable labeling-substance modified with a second binding substance that specifically binds to the substance to be detected or by a third binding substance that specifically binds to the first binding substance and that competes with the substance to be detected, wherein
 the photo reactable labeling substance includes a plurality of molecules of photo reactable substance enclosed by a light transmissive material that transmits light output from the plurality of molecules of the photo reactable substance to prevent metal quenching that occurs when the photo reactable substance is located close to the metal layer.

16. A kit for detecting an optical signal, as defined in claim 15, wherein the particle diameter of the photo-reactable labeling-substance is less than or equal to 5300 nm.

17. A kit for detecting an optical signal, as defined in claim 15, wherein the particle diameter of the photo-reactable labeling-substance is in the range of 70 nm to 900 nm.

18. A kit for detecting an optical signal, as defined in claim 15, wherein the photo-reactable substance produces fluorescence by irradiation with the excitation light, and wherein the particle diameter of the photo-reactable labeling-substance is in the range of 90 nm to 700 nm.

19. A kit for detecting an optical signal, as defined in claim 15, wherein the photo-reactable substance produces fluorescence by irradiation with the excitation light, and wherein the particle diameter of the photo-reactable labeling-substance is in the range of 130 nm to 500 nm.

20. A kit for detecting an optical signal, as defined in claim 15, wherein the photo-reactable substance produces fluorescence by irradiation with the excitation light, and wherein a metal coating is provided on the surface of the photo-reactable labeling-substance in such a manner that the thickness of the metal coating is sufficiently thin to transmit the fluorescence.

* * * * *